United States Patent
Muni et al.

(10) Patent No.: US 11,564,909 B2
(45) Date of Patent: Jan. 31, 2023

(54) METHODS AND COMPOSITIONS FOR ORAL PILOCARPINE LIQUID

(71) Applicant: ROMEG Therapeutics LLC, Woburn, MA (US)

(72) Inventors: Indu Muni, North Reading, MA (US); Naomi Vishnupad, Reading, MA (US)

(73) Assignee: ROMEG Therapeutics LLC, Woburn, MA (US)

( * ) Notice: Subject to any disclaimer, the term of this patent is extended or adjusted under 35 U.S.C. 154(b) by 0 days.

(21) Appl. No.: 17/536,632

(22) Filed: Nov. 29, 2021

(65) Prior Publication Data

US 2022/0175733 A1 Jun. 9, 2022

Related U.S. Application Data

(60) Provisional application No. 63/119,232, filed on Nov. 30, 2020.

(51) Int. Cl.
| | | |
|---|---|---|
| *A61K 31/4178* | (2006.01) | |
| *A61K 47/10* | (2017.01) | |
| *A61K 47/12* | (2006.01) | |
| *A61K 47/26* | (2006.01) | |
| *A61K 47/34* | (2017.01) | |
| *A61K 47/38* | (2006.01) | |
| *A61K 9/00* | (2006.01) | |

(52) U.S. Cl.
CPC ........ *A61K 31/4178* (2013.01); *A61K 9/0053* (2013.01); *A61K 47/10* (2013.01); *A61K 47/12* (2013.01); *A61K 47/26* (2013.01); *A61K 47/34* (2013.01); *A61K 47/38* (2013.01)

(58) Field of Classification Search
CPC ...... A61K 31/375; A61K 33/04; A61K 33/32; A61K 33/34; A61K 45/06
See application file for complete search history.

(56) References Cited

U.S. PATENT DOCUMENTS

| | | | | |
|---|---|---|---|---|
| 3,856,919 A | * | 12/1974 | Rankin | ................... C08L 71/02 514/422 |
| 4,209,505 A | | 6/1980 | Mikhail | |
| 2006/0029665 A1 | * | 2/2006 | Singh | ........................ A61P 1/00 424/464 |
| 2007/0053995 A1 | | 3/2007 | Paborji | |
| 2008/0254101 A1 | | 10/2008 | Singh | |
| 2010/0062975 A1 | * | 3/2010 | Houck | ................ A61K 31/4178 530/321 |
| 2013/0157963 A1 | * | 6/2013 | Gore | ........................ A61P 27/02 514/249 |
| 2015/0132372 A1 | | 5/2015 | Benameur et al. | |
| 2017/0239243 A1 | * | 8/2017 | Khopade | ............... A61K 9/0051 |
| 2018/0098938 A1 | | 4/2018 | Muni et al. | |
| 2019/0060462 A1 | * | 2/2019 | Tengler | ................. A61K 9/4866 |

OTHER PUBLICATIONS

Artursson et al.: Caco-2 monolayers in experimental and theoretical predictions of drug transport. Adv. Drug Deliv. Rev. 46:27-43 (2001).
Balimane, P.V.: Current Industrial Practices of Assessing Permeability and P-Glycoprotein Interaction. AAPS J. 8(1):E1-E13 (2006).
Endres et al.: The role of transporters in drug interactions. Eur. J. Pharm. Sci. 27:501-517 (2006).
Fawcett et al.: Formulation and stability of pilocarpine oral solution. Article first published online: Feb. 22, 2011 DOI: 10.1111/j.2042-7174.1994.tb00780.x.
Ferguson et al.: Pilocarpine oral solution. Br Dent J. 170:251 (1991).
Giacomini et al.: Membrane transporters in drug development. The International Transporter Consortium, White Paper. Nature Reviews Drug Discovery. 9:215-236 (2010).
Stewart et al.: Comparison of intestinal permeabilities determined in multiple in vitro and in situ models: relationship to absorption in humans. Pharm. Res. 12:693-699 (1995).
Yee, Shiyin: In Vitro Permeability across Caco-2 Cells (Colonic) Can Predict In Vivo (Small Intestinal) Absorption in Man—Fact or Myth. Pharm. Res 14(6):763-766 (1997).
PCT/US2021/060970 International Search Report and Written Opinion dated Jun. 29, 2022.

* cited by examiner

*Primary Examiner* — Jared Barsky
(74) *Attorney, Agent, or Firm* — Wilson Sonsini Goodrich & Rosati

(57) ABSTRACT

Liquid oral pilocarpine formulations are described herein. Methods of using the liquid oral pilocarpine formulations are also provided.

20 Claims, 5 Drawing Sheets

METHODS AND COMPOSITIONS FOR ORAL PILOCARPINE LIQUID

CROSS REFERENCE

This application claims the benefit of U.S. Provisional Application No. 63/119,232, filed Nov. 30, 2020, which is herein incorporated by reference in its entirety.

BACKGROUND

Pilocarpine, a nonselective muscarinic agonist, is a saliva production stimulator. It has been used to treat dry mouth caused by radiation treatment or Sjögren syndrome as well as to reduce pressure in the eye from glaucoma. In ophthalmology, pilocarpine is also used to reduce the possibility of glare at night from lights when the patient has undergone implantation of phakic intraocular lenses.

Oral pilocarpine is usually delivered in the form of a solid oral dosage such as a tablet or capsule that is swallowed. For example, SALAGEN® (MGI Pharma, Inc) is a tablet for oral administration containing pilocarpine hydrochloride. The delivery of pilocarpine as a solid oral dosage form is not optimal, particularly in patients that have trouble swallowing tablets.

SUMMARY

Described herein are methods of treating a pilocarpine sensitive disorder, comprising orally administering a liquid pilocarpine formulation to a subject having a pilocarpine sensitive disorder in an effective amount to treat the disorder. In some embodiments, the pilocarpine sensitive disorder is selected from dry mouth, xerostomia, oral mucositis, dry eye, and Sjögren's syndrome. In some embodiments, the pilocarpine sensitive disorder is dry mouth. In some embodiments, the pilocarpine sensitive disorder is xerostomia. In some embodiments, the pilocarpine sensitive disorder is oral mucositis. In some embodiments, the pilocarpine sensitive disorder is Sjögren's syndrome. In some embodiments, the pilocarpine sensitive disorder is dry eye. In some embodiments, the subject is human.

Disclosed herein are pharmaceutical solutions and pharmaceutical suspensions suitable for oral administration comprising pilocarpine or its salts and a pharmaceutically acceptable solvent system comprised of one or more agents selected from the group consisting of water, glycols, buffering agents, sweeteners, flavoring agents, preservatives and dyes.

In some embodiments the solution comprises about 0.4-0.6% (w/v) citric acid (anhydrous). In some embodiments, the solution comprises about 10-30% (w/v) glycerin. In some embodiments, the solution comprises about 2-8% (w/v) propylene glycol. In some embodiments, the sweetener is about 0.01-0.02% (w/v) sucralose. In some embodiments, the flavoring agent is about 0.03-0.05% (w/v) Flavor Grape 59266/A and/or Flavor Cherry 825.662. In some embodiments, the solution comprises about 0.05-0.3% w/v hydroxyethylcellulose (Natrasol 250HHX). In some embodiments, the solution comprises about 0.25-0.75% w/v of poloxamer 407. In some embodiments, the solution comprises about 0.01-0.2% w/v of simethicone emulsion. In some embodiments, the solution comprises about 0.2-0.4% w/v of sodium citrate, dihydrate. In some embodiments, the solution comprises about 0.1-0.2% w/v of sodium benzoate. In some embodiments, the solution comprises about 12-18% w/v of sorbitol solution (70%). In some embodiments, the dye comprises about 0.0004-0.0008% w/v of FD&C Blue No. 1. In some embodiments, the dye comprises about 0.001-0.003% w/v of FD&C Red No. 40. In some embodiments, the solution comprises FD&C Blue No. 1 and FD&C Red No. 40. In some embodiments, the solution does not contain sorbitol. In some embodiments, the solution does not contain a dye. In some embodiments, the solution does not contain either sorbitol or a dye In some embodiments, the solution comprises about 0.01-0.2% w/v of pilocarpine HCl. In some embodiments, the solution comprises 0.1% w/v of pilocarpine HCl. In some embodiments, the concentration of pilocarpine in the solution is 0.1 mg-2.0 mg/mL.

In some embodiments, the pharmaceutically acceptable solvent system is comprised of one or more agents selected from the group consisting of water, propylene glycol, glycerin, hydroxyethylcellulose (Natrasol 250HHX), sodium citrate, dihydrate, poloxamer 407, citric acid, sodium benzoate, simethicone emulsion, sucralose, sorbitol solution (70%), a dye, and a flavoring agent and/or taste enhancing agent.

In some embodiments, the pharmaceutically acceptable solvent system is comprised of the following components: 0.5% w/v of citric acid, anhydrous, 0.0006% w/v of FD&C Blue No. 1, 0.002% w/v of FD&C Red No. 40, 0.04% w/v of Flavor Grape 59266/A, 15% w/v of glycerin, 0.2% w/v of hydroxyethylcellulose (Natrasol 250HHX), 0.1% w/v of pilocarpine HCl, 0.5% w/v of poloxamer 407, 5% w/v of propylene glycol, 0.1% w/v of simethicone emulsion, 0.3% w/v of sodium citrate, dihydrate, 0.15% w/v of sodium benzoate, 15% w/v of sorbitol solution (70%), 0.015% w/v of sucralose, and purified water. In some embodiments, the pharmaceutically acceptable solvent system is comprised of the following components: 0.5% w/v of citric acid, anhydrous, 0.0005% w/v of FD&C Blue No. 1, 0.0015% w/v of FD&C Red No. 40, 0.04% w/v of Flavor Grape 59266/A, 20% w/v of glycerin, 0.2% w/v of hydroxyethylcellulose (Natrasol 250HHX), 0.1% w/v of pilocarpine HCl, 0.5% w/v of poloxamer 407, 5% w/v of propylene glycol, 0.05% w/v of simethicone emulsion, 0.35% w/v of sodium citrate, dihydrate, 0.15% w/v of sodium benzoate, 0.015% w/v of sucralose, and purified water.

Also disclosed herein are liquid oral pilocarpine solutions and liquid oral pilocarpine suspensions that are stable for 30 days to 24 months at ambient and refrigerated temperature conditions.

In some embodiments, the liquid oral solution or suspension or pharmaceutical solution or suspension is stable for up to 24 months at ambient conditions. In some embodiments, the liquid oral solution or suspension or pharmaceutical solution or suspension is stable for 6 or more months at accelerated conditions. In some embodiments, the pH of the liquid oral solution or suspension or pharmaceutical solution or suspension is stable. In some embodiments, the liquid oral solution or suspension or pharmaceutical solution or suspension has a viscosity in the range of 40-800 cps. In some embodiments, the liquid oral solution or suspension or pharmaceutical solution or suspension has a viscosity of 80-300 cps. In some embodiments, pH range of the solution is 3-6. In some embodiments, the pH range of the solution is 3.5-5.5. In some embodiments, the pH of the solution is 4.2-4.8.

In some embodiments, the liquid oral solution or suspension or pharmaceutical solution or suspension, has less than 5% of any one degradant.

In some embodiments, the oral solution or suspension does not include boric acid. In some embodiments, the oral solution or suspension does not include benzalkonium chloride. In some embodiments, the oral solution or suspension is non-sterile.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5A shows a chromatogram of a 5.0 mg pilocarpine tablet. FIG. 5B shows a chromatogram of a 7.5 mg pilocarpine tablet. FIG. 5C shows a chromatogram of pilocarpine liquid. Propranolol was utilized as an analytical internal standard for the mass spectrometry injections.

DETAILED DESCRIPTION OF THE INVENTION

Figure 1:
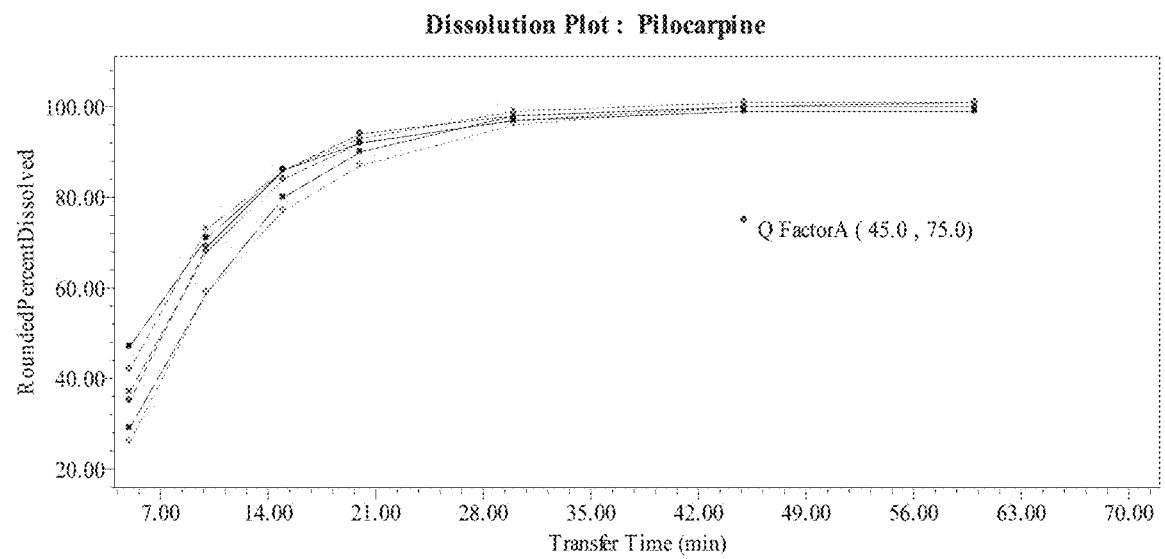
FIG. 1 depicts a dissolution plot for pilocarpine hydrochloride tablets, 5 mg corresponding to the data presented in Table 9.

Disclosed herein are pilocarpine oral solution formulations. These oral solutions are intended for ingestion. Pilocarpine, a cholinergic agonist, stimulates certain nerves to increase the amount of saliva one produces, to allow for more comfortable speech and swallowing. Pilocarpine is a nonselective muscarinic agonist and can therefore be used to treat dry mouth (e.g., caused by radiation treatment, caused by side effects of other medications, or caused by Sjögren's syndrome). It can also reduce pressure in the eye from glaucoma. In ophthalmology, pilocarpine is also used to reduce the possibility of glare at night from lights after a patient has undergone implantation of phakic intraocular lenses. It can also be used for the treatment of dry eye. Pilocarpine is used to stimulate sweat glands in a sweat test to measure the concentration of chloride and sodium that is excreted in sweat. It is also used to diagnose cystic fibrosis. Pilocarpine may also be used to minimize severity of oral mucositis symptoms. Pilocarpine is currently administered to patients as a tablet or capsule, mouthwash, or via eye drops (i.e. for dry mouth, dry eye, or xerostomia). Oral ingestible solutions are not available. Pilocarpine, as a liquid, can also be administered by transport across the mucous membranes. Solutions in the market are either toxic for ingestion and not formulated to be ingested or unstable and therefore produced via pharmaceutical compounding methods. In some embodiments, the patient or subject is a mammal (e.g., a dog, a cat, or a mouse). In some embodiments, the subject is a primate. In some embodiments, the subject is human.

Commercial oral solutions of pilocarpine have not been previously developed due to problems associated with the integrity of the solution. The solution of the instant application provides a stable solution, that is capable of being stored at room temperature for at least two years, is non-toxic with a pleasant taste for easy administration through ingestion, and is a solution with unexpected permeability, that is better than the permeability of pilocarpine tablets. Pilocarpine has been shown to be unstable at room temperature in solution (Fawcett et al.). Pilocarpine mouth rinse solutions need to be stored in cool, dry places, and must be disposed of after limited times (e.g., GLANDOMED® mouth rinse solution). Not only are these forms of pilocarpine solution sensitive to high temperatures, they are also unstable at cold temperatures. The stability of pilocarpine oral solution tested after storage for 90 days at 4, 25 and 38 C was assed. Solutions prepared from a pH 7.5 phosphate buffer were found to have significant decomposition at all temperature points (Fawcett et al.). Additionally, many pilocarpine formulations, specifically eye drops, apart from having a bitter unpleasant taste cannot be ingested as they include toxic ingredients such as boric acid and benzalkonium chloride.

Many researchers have reported on pilocarpine hydrochloride mouthwash/mouth rinse products. In order to be effective, all these products contain much larger doses of pilocarpine hydrochloride (20 to 40×) compared to the currently FDA approved tablets, which are prescribed at a 5 mg oral dose BID or QID. Because of the higher concentrations of pilocarpine hydrochloride, the product may be harmful and even fatal if swallowed accidentally. These formulations are ⅕ to 1/10 less effective than oral tables because of limited drug absorption from the oral cavity. This is problematic for patients experiencing dry mouth since these patients often have dysphasia causing them to accidentally swallow the mouth wash. No reliable stability information is available for these liquid formulations. Pilocarpine eye drops are available as 10 mg/mL, 20 mg/mL and 40 mg/mL solutions. Logistically, one cannot accurately measure a correct oral dosage from an eye drop. Moreover, eye drops contain permeation enhancers such as polyoxyethylene glycol, ethers (e.g. lauryl, stearyl, and oleyl), EDTA, DMSO, sodium taurocholate, and Cremaphor E which are not suitable for oral ingestion.

Pilocarpine has been compounded for veterinary use. It is not approved by the FDA for veterinary use. The compounded veterinary pilocarpine HCl usually contain preservatives (e.g. Wedgewood Pharmacy). These products are compounded due to the unstable nature of pilocarpine solutions, and should be discarded 90 days after being compounded.

It was unexpected that formulations described herein can be stable for at least 2 years. The oral solutions listed herein are stable for commercial acceptability and meet all scientific and regulatory stability standards. In addition, these solutions have been designed to be user-friendly (i.e. to have a pleasant taste) which helps with patient compliance.

Pilocarpine use may result in a range of adverse effects, most related to its non-selective action as a muscarinic receptor agonist. Pilocarpine has been known to cause excessive salivation, sweating, bronchial mucus secretion, bronchospasm, bradycardia, vasodilation, runny nose, chills, flushing, frequent urge to urinate, dizziness, weakness, blurred vision, and diarrhea. Additional symptoms, primarily from eye drops, may include brow ache and chronic use in miosis.

Pilocarpine, (3S,4R)-3-Ethyl-4-((1-methyl-1H-imidazol-5-yl)methyl)dihydrofuran-2(3H)-one, is made from plants in the genus *Pilocarpus*. It is extracted from the powdered leaves of *Pilocarpus microphyllus*. The invention encompasses liquid formulations of pilocarpine. The present invention provides for liquid formulation of pilocarpine, suitable for oral administration that is stable at room temperature. The liquid formulation can be either a solution or a suspension.

Some of the challenges in formulating an oral liquid of pilocarpine include maintaining stability of the pilocarpine (e.g., in high temperatures), delivery for systemic absorption, and maintaining an optimum pH. It is also important to establish an effective preservative system to prevent the growth of bacteria, mold, and other contaminants. Additionally, the oral liquid pilocarpine must be patient friendly and requires suitable packaging, such as a container closure system that factors in the potential effects of light and air exposure.

Also provided herein are methods of treating dry mouth or xerostomia due to a certain immune disease (e.g. Sjögren's syndrome), as a side effect of a medication or medical treatments, or as a side effect or from saliva gland damage due to radiation treatments of the head/neck for cancer, and ophthalmic conditions (e.g., dry eye) comprising administering to a patient, such as a child or an elderly patient, an oral liquid formulation comprising pilocarpine as described herein. Pilocarpine is a cholinergic parasympathomimetic agent, increasing secretion by the exocrine glands, and can produce contraction of the iris sphincter muscle and ciliary muscle (when topically applied to the eyes) by stimulating muscarinic receptors. In some embodiments, oral liquid formulations disclosed herein can also be used to treat other conditions known in the art.

Commonly, geriatric populations encounter difficulty being administered solid oral dosage forms such as tablets and capsules. This may lead to non-compliance with the recommended pharmacotherapy with the solid oral dosage forms and likely results in rendering the therapy ineffective. Solid oral dosage forms are usually not favorable for geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released.

As used herein, "pilocarpine" refers to pilocarpine base ((3S,4R)-3-Ethyl-4-((1-methyl-1H-imidazol-5-yl)methyl) dihydrofuran-2(3H)-one), its salt, or solvate or derivative or isomer or polymorph thereof. Suitable compounds include the free base, the organic or inorganic salts, isomers, isomer salts, solvates, polymorphs, complexes, etc. Pilocarpine can be found in crystalline form as pilocarpine hydrochloride. Exemplary structures of pilocarpine and pilocarpine hydrochloride can be found below.

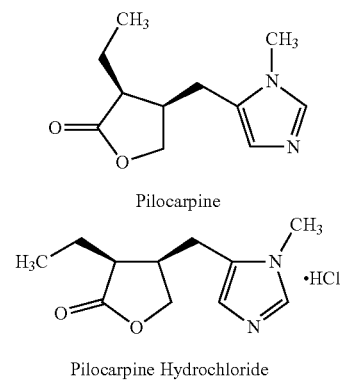

In some embodiments the oral liquid pilocarpine formulation is stable at room temperature for at least 3 months, at least 6 months, at least 12 months, at least 18 months, or at least 24 months. In some embodiments the oral liquid pilocarpine formulation is stable at accelerated temperatures for at least 1 month, at least 2 months, at least 3 months, or at least 6 months. In some embodiments the oral liquid pilocarpine formulation is determined to be stable when the solution has less than 9%, less than 8%, less than 7%, less than 6%, less than 5%, less than 4%, less than 3%, less than 2%, less than 1% or less than 0.5% of any one degradant. In other embodiments the oral liquid pilocarpine formulation is determined to be stable when the solution has less than 9%, less than 8%, less than 7%, less than 6%, less than 5%, less than 4%, less than 3%, less than 2%, less than 1% or less than 0.5% of total degradants. Pilocarpine degradants are known in the art (i.e., isopilocarpine, pilocarpic acid, and isopilocarpic acid).

The pilocarpine is a therapeutic agent having a pharmaceutical, pharmacological, or therapeutic effect. Pilocarpine used in the solutions or suspensions described herein may be any type of pharmaceutically acceptable form of the drug. For example, pilocarpine can be in a racemic or isomeric mixture, a solid complex bound to an ion exchange resin, or the like. In addition, pilocarpine can be in a solvated form. The term "pilocarpine" is also intended to include all pharmaceutically acceptable salts, derivatives, analogs, and extracts of the drug, as well as combinations thereof. For example, the pharmaceutically acceptable salts of pilocarpine include, without limitation, the acetate, succinate, tartrate, bitartrate, dihydrochloride, salicylate, hemisuccinate, citrate, maleate, hydrochloride, carbamate, sulfate, nitrate, and benzoate salt forms thereof, as well as combinations thereof and the like. For instance suitable pharmaceutically acceptable salts of pilocarpine include, without limitation, pilocarpine hydrochloride, pilocarpine nitrate, pilocarpine sulfate, pilocarpine acetate, pilocarpine citrate, pilocarpine tartrate, pilocarpine zinc chloride monohydrate, pilocarpine salicylate, a concentrated extract of *Pilocarpus* leaves, and combinations thereof.

Dry Mouth or Xerostomia

Dry mouth or xerostomia is common and is often a side effect of various types of medication. Xerostomia and dry mouth are characterized by dryness in the mouth that can be associated with a change in saliva composition, hyposalivation, or may have no identifiable cause. Dehydration, radiotherapy (involving salivary glands) and other diseases can cause hyposalivation or oral mucositis. Other causes of dry mouth or xerostomia include Sicca syndrome, Sjogren's syndrome, physiologic causes (e.g., sleep), drug-induced effects of medication, and other causes.

Pilocarpine is used for treating Sjogren's syndrome (SS), as it is a disease which results in dry mouth. SS consists of autoimmune damage to the salivary gland. Pilocarpine can be used for treating adults with dry mouth or xerostomia. In some embodiments, oral liquid formulations disclosed herein are used to treat dry mouth or xerostomia.

Ophthalmic Applications

Pilocarpine is used in ocular applications primarily for reduction of elevated intraocular pressure (TOP). It can also be used for miosis, constriction of the pupil. Patients with IOP can be suffering from open-angle glaucoma or ocular hypertension. Pilocarpine can also be administered prior to laser eye surgery for the prevention of postoperative elevated IOP. Frequency and concentration of pilocarpine can be determined by the severity of the elevated IOP and also by the miotic response of a subject. In some embodiments, pilocarpine can be prescribed to reduce the amount of fluid in the eye, which can decrease pressure inside the eye.

Glaucoma causes damage to the eye's optic never over time. Risk factors for glaucoma include increased pressure in the eye. Pilocarpine has been used for open angle and narrow angle glaucoma. In some embodiments, oral liquid formulations disclosed herein are used to treat glaucoma, ocular hypertension, or other ophthalmic conditions associated with elevated IOP.

In some embodiments, the pilocarpine oral solution can be used to treat dry eye.

Formulations

The liquid formulations described herein may include additional ingredients. For instance these additional components may include, but are not limited to, buffering agents, preservatives, sweeteners, flavoring agents, glycols such as propylene glycol and glycerin, as examples, and coloring agents. Additional excipients such as tonicity agents and chelating agents are within the scope of the embodiments. The liquid formulations described herein do not include substances that are toxic if ingested (e.g. boric acid and benzalkonium chloride).

Buffering agents maintain the pH when pilocarpine is compounded into a liquid form. Non-limiting examples of buffering agents include, but are not limited to, sodium bicarbonate, potassium bicarbonate, magnesium hydroxide, magnesium lactate, magnesium gluconate, aluminum hydroxide, aluminum hydroxide/sodium bicarbonate precipitate, a mixture of an amino acid and a buffer, a mixture of aluminum glycinate and a buffer, a mixture of acid salt and an amino acid and a buffer, and a mixture of an alkali salt of an amino acid and a buffer. Additional buffering agents include citric acid, sodium citrate, sodium tartarate, sodium acetate, sodium carbonate, sodium polyphosphate, potassium polyphosphate, sodium pyrophosphate, potassium pyrophosphate, disodium hydrogen phosphate, dibasic sodium phosphate, trisodium phosphate, tripotassium phosphate, sodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is compounded into a liquid. In some embodiments, the pilocarpine oral solution described herein, comprises a buffering agent. In some embodiments the pH of the liquid solution is between 3-6. In some embodiments, the pH is between 3.5-5.5. In a preferred embodiment, the pH is between 4.2-4.8 In some embodiments, the formulations described herein have a stable pH. In some embodiments, the formulations described herein maintain the same pH range established at time zero over a stability testing period. The stability testing period may be 3 months at accelerated testing conditions or between 12 and 24 months at room temperature.

Preservatives include anti-microbials, anti-oxidants, and agents that enhance sterility. Exemplary preservatives include ascorbic acid, ascorbyl palmitate, benzyl alcohol, BHA, BHT, citric acid, erythorbic acid, fumaric acid, malic acid, propyl gallate, sodium ascorbate, sodium benzoate, sodium bisulfate, sodium metabisulfite, sodium sulfite, parabens (methyl-, ethyl-, butyl-), benzoic acid, potassium sorbate, and vanillin. In some embodiments, the pilocarpine oral solution described herein, comprises a preservative.

Sweeteners or sweetening agents include any compounds that provide a sweet taste to make the product more palatable. This includes natural and synthetic sugars, natural and artificial sweeteners (e.g., sucralose), natural extracts and any material that initiates a sweet sensation in a subject. In some embodiments, the pilocarpine oral solution described herein, comprises a sweetener. In other embodiments, sweeteners in liquid form are used to solvate or dissolve the pilocarpine described herein.

Sugars illustratively include glucose, fructose, sucrose, xylitol, tagatose, maltitol, isomaltulose, lactitol, sorbitol, mannitol, erythritol, trehalose, maltodextrin, polydextrose, and the like. Other sweeteners include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, and as branded proprietary blend products. Sweeteners can be used singly or combinations of two or more. Suitable concentrations of different sweeteners can be selected based on published information, manufacturers' data sheets, and by routine testing. In certain instances, an above-described flavored solution component is used to solvate or dissolves pilocarpine described herein.

In another embodiment, the liquid form comprises a flavoring agent or flavorant to enhance the taste or aroma of the solution component used to solvate or dissolve the pilocarpine described herein. Suitable natural or synthetic flavoring agents can be selected from standard reference books, such as Remington: The Science and Practice of Pharmacy (2000) and Fenaroli's Handbook of Flavor Ingredients (1994). Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. Also useful, particularly where the composition is intended primarily for pediatric use is tutti-frutti or bubble gum flavor, a compounded flavoring agent based on fruit flavors. Presently, preferred flavoring agents include bubble gum, strawberry, cherry, grape, orange, peppermint, and vanilla. In some embodiments, the resultant liquid form from the pilocarpine described herein comprises a Flavor Cherry 825.662 and/or Flavor Grape 59266/A flavoring agent. Flavoring agents may be used singly or in combinations of two or more.

In further embodiments, the resultant liquid form from the pilocarpine described herein comprises a coloring agent for identity and/or aesthetic purposes. Suitable coloring agents approved by the U.S. Food and Drug Administration (FDA) include FD&C Red No. 3, FD&C Red No. 20, FD&C Red No. 40, FD&C Yellow No. 6, FD&C Blue No. 1, FD&C Blue No. 2, D&C Green No. 5, D&C Orange No. 5, D&C Yellow No. 10, caramel, ferric oxide and mixtures thereof. In some embodiments, the formulations described herein do not contain dyes or colorants.

In further embodiments, the resultant liquid form from the pilocarpine described herein comprises a thickening agent. Thickening agents include, but are not limited to xanthan gum, sodium alginate, methylcellulose, hydroxyethylcellulose, hydroxypropylcellulose, hydroxypropylmethylcellulose, CMC, Na-CMC, microcrystalline cellulose, tragacanth, bentonite, carageenan, guar gum, and colloidal silicon dioxide. In some embodiments, hydroxyethylcellulose (Natrasol 250HHX) is used.

In some embodiments other flavoring agents, buffering systems, and preservatives may be used. The solution is formulated to inhibit growth of bacteria, mold, and yeast for storage at room temperature and ambient conditions. In some embodiments, surfactants are used in the solution. In some embodiments, surfactants such as poloxamer 407 are used. In some embodiments, the solutions and suspensions described herein comprise a surfactant or wetting agent selected from the group consisting of alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, poloxamer 237, poloxamer 338, poloxamer 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and combinations thereof. In some embodiments, the solution includes anti-foaming agents such as simethicone and simethicone emulsion. In some embodiments, the solutions and suspensions described herein comprise a humectant selected from the group consisting of glycerin, hexylene glycol, propylene glycol, and sorbitol. In some embodiments, glycerin can be used to produce humectant properties. In some embodiments, the pilocarpine solution or suspension is non-sterile.

In some embodiments, the liquid formulation, by % w/v, can be found in Table 1. In other embodiments, the formulation includes 0.4-0.6% w/v of citric acid, anhydrous, 0.0004-0.0008% w/v of FD&C Blue No. 1, 0.001-0.003% w/v of FD&C Red No. 40, 0.03-0.05% w/v of Flavor Grape 59266/A, 10-30% w/v of glycerin, 0.05-0.3% w/v of hydroxyethylcellulose (Natrasol 250HHX), 0.01-0.2% w/v of pilocarpine HCl, 0.25-0.75% w/v of poloxamer 407, 2-8% w/v of propylene glycol, 0.01-0.2% w/v of simethicone emulsion, 0.2-0.45% w/v of sodium citrate, dihydrate, 0.1-0.2% w/v of sodium benzoate, 12-18% w/v of sorbitol solution (70%), 0.01-0.02% w/v of sucralose, and purified water. In other embodiments, the formulation includes 0.5% w/v of citric acid, anhydrous, 0.0006% w/v of FD&C Blue No. 1, 0.0015% w/v of FD&C Red No. 40, 0.04% w/v of Flavor Grape 59266/A, 20% w/v of glycerin, 0.2% w/v of hydroxyethylcellulose (Natrasol 250HHX), 0.1% w/v of pilocarpine HCl, 0.5% w/v of poloxamer 407, 5% w/v of propylene glycol, 0.05% w/v of simethicone emulsion, 0.35% w/v of sodium citrate, dihydrate, 0.15% w/v of sodium benzoate, 15% w/v of sorbitol solution (70%), 0.015% w/v of sucralose, and purified water.

TABLE 1

Exemplary formulation

| Item # | Ingredient | % w/v |
|---|---|---|
| 1 | Pilocarpine HCl | 0.1000 |
| 2 | Hydroxyethylcellulose (Natrasol 250 HHX) | 0.2000 |
| 3 | Citric Acid, Anhydrous, USP | 0.5000 |
| 4 | FD&C Red No. 40 | 0.0015 |
| 5 | FD&C Blue No. 1 | 0.0005 |
| 6 | Flavor Grape 59266/A | 0.0400 |
| 7 | Glycerin, USP | 20.0000 |
| 8 | Propylene Glycol, USP | 5.0000 |
| 9 | Poloxamer 407 | 0.5000 |
| 10 | Simethicone Emulsion | 0.0500 |
| 11 | Sodium Citrate, Dihydrate | 0.3500 |
| 12 | Sodium Benzoate, NF | 0.1500 |
| 13 | Sucralose, NF | 0.0150 |
| 14 | Sorbitol Solution 70% | 15.0000 |
| 15 | Purified Water, USP | QS |

Storage

The pilocarpine solutions and suspensions described herein are stable in various storage conditions including refrigerated, ambient, and accelerated conditions. Stable as used herein refers to the ability of an active agent to maintain activity under standard stability conditions. Standard stability conditions include relative humidity conditions along with the temperatures, 25° C. 60% RH(RT), 30° C. 65% RH (ICH), and 40° C. 75% RH (accelerated), for example.

At refrigerated and ambient conditions, the liquid pilocarpine composition described herein in stable for at least 1 month, at least 2 months, at least 3 months, at least 6 months, at least 9 months, at least 12 months, at least 15 months, at least 18 months, or at least 24 months. At accelerated conditions, the pilocarpine solution described herein is stable for at least 1 month, at least 2 months, at least 3 months, or at least 6 months. Accelerated conditions include temperatures that are above ambient levels. In some instances, an accelerated condition is at about 30° C., about 35° C., about 40° C., about 45° C., about 50° C., about 55° C., or about 60° C. Ambient conditions include temperature that is at ambient levels. In some instances, an ambient condition is at about 20° C., about 21° C., about 22° C., about 23° C., about 24° C., about 25° C., about 26° C., about 27° C., about 28° C., about 29° C., and about 30° C. Refrigerated conditions include temperature in typical refrigeration units (e.g. 5±3° C.). In some instances, a refrigerated condition is about 2° C., about 3° C., about 4° C., about 5° C., about 6° C., about 7° C., or about 8° C.

Liquid vehicles suitable for the pilocarpine described herein are selected for a particular oral liquid composition (e.g., solution, suspension, etc.) as well as other properties such as clarity, viscosity, compatibility with excipients, chemical inertness, palatability, odor, and color. Exemplary liquid vehicles include water, ethyl alcohol, glycerin, propylene glycol, syrup (e.g., sugar or other sweetener based, e.g., ORA-SWEET® SF sugar-free flavored syrup), juices (e.g., apple, orange, cranberry, cherry, tomato and the like), other beverages (e.g., tea, coffee, soft drinks, milk and the like), oils (e.g., olive, soybean, corn, mineral, castor and the like), and combinations or mixtures thereof. Certain liquid vehicles, e.g., oil and water, can be combined together to form emulsions. In some embodiments, water is used as a vehicle for a pilocarpine oral liquid. In other embodiments, propylene glycol is used as a vehicle for a pilocarpine oral liquid. For the liquid pilocarpine described herein, the solution component is used as the vehicle for a pilocarpine oral liquid.

The viscosity of the solution is an important component. In some embodiments the solution has a viscosity in the range of 40-800 cps. In other embodiments the solution has a viscosity of 80-300 cps.

The pilocarpine oral liquid compositions may be used for the treatment of diseases and conditions described herein. In addition, a method for treating any of the diseases or conditions described herein in a subject in need of such treatment involves administration of pilocarpine oral liquid compositions in therapeutically effective amounts to the subject. In some embodiments, the amount of a given pilocarpine oral liquid composition that corresponds to such an amount varies depending on factors such as the particular pilocarpine salt or form, disease condition and its severity, the identity (age, weight, sex) of the subject or patient in need of treatment, but can nevertheless be determined according to the particular circumstances surrounding the case, including, e.g., the specific agent being administered, the liquid composition type, the condition being treated, and the subject or patient being treated.

Thus, the term "therapeutically effective amount" refers to the amount of pilocarpine or a pharmaceutically acceptable salt thereof that is capable of achieving a therapeutic effect in a subject in need thereof. For example, a therapeutically effective amount of pilocarpine or a pharmaceutically acceptable salt thereof can be the amount that is capable of preventing or relieving one or more symptoms associated with dry mouth or the other indications described herein (pilocarpine sensitive disorders).

The oral solution described herein has sufficient bioavailability to treat pilocarpine sensitive disorders. "Bioavailability" refers to the rate and/or extent to which a drug is absorbed or becomes available to the treatment site in the body.

In some embodiments, the pilocarpine solution has between 0.5 mg-2.0 mg of pilocarpine per 1 mL of solution. In some embodiments, the pilocarpine solution has 0.5, 0.6, 0.7, 0.8, 0.9, 1.0, 1.1, 1.2, 1.3, 1.4, 1.5, 1.6, 1.7, 1.8, 1.9, or 2.0 mg of pilocarpine per 1 mL of solution. In some embodiments, the pilocarpine solution has 1 mg of pilocarpine per mL of solution.

In further embodiments, the daily dosages appropriate for the pilocarpine oral liquid compositions described herein are from about 0.5 mg-10.0 mg/dose of pilocarpine for up to 10 doses/day. In some embodiments, compositions herein are administered more than 10 times a day. In one embodiment, the daily dosage appropriate for the pilocarpine liquid composition is about 3.0 mg-7.0 mg of pilocarpine/dose. In some embodiments, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg or 10 mg of pilocarpine are administered per dose. In some embodiments, 1, 2, 3, 4, 5, 6, 7, 8, 9, or 10 doses of pilocarpine are administered per day. In some embodiments the dosage of pilocarpine administered to a subject is between 0.1 mg to 50 mg per day. In other embodiments, the dosage is between 1.0 mg to 50 mg per day. Other dose ranges include between 5 to 50 mg, between 10 to 40 mg, and between 15 to 25 mg per day. The dose may also be at 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 20 mg, 25 mg, 30 mg, 35 mg, 40 mg, 45 mg, or 50 mg per day. In a preferred embodiment, 5 mg of pilocarpine is administered three times a day. In another preferred embodiment, 5 mg of pilocarpine is administered four times a day. In some embodiments, 5 mL of pilocarpine solution is administered three times a day. In some embodiments, 5 mL of pilocarpine solution is administered four times a day.

The treatment of certain diseases or conditions (e.g., dry mouth, oral mucositis, etc.) in a patient or subject with a pilocarpine oral liquid composition described herein encompass additional therapies and treatment agents in some embodiments. Such additional therapies and treatment regimens include another therapy, e.g., antibiotics, for the treatment of the particular disease, in some embodiments.

Unless defined otherwise, all technical and scientific terms used herein have the same meanings as commonly understood by one of ordinary skill in the art. Although any methods and materials similar or equivalent to those described herein can be used in the practice of testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent, such as liquid oral pilocarpine, is directed to the treatment and/or the amelioration of, reversal of, or stabilization of the symptoms of dry mouth, oral mucositis, xerostomia, Sjogren's syndrome, glaucoma, ocular hypertension, dry eye, and other diseases described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an oral liquid pilocarpine composition, can include, but is not limited to, providing an oral liquid pilocarpine composition into or onto the target tissue; providing an oral liquid pilocarpine composition systemically to a patient by, e.g., oral administration whereby the therapeutic reaches the target tissue or cells. "Administering" a composition may be accomplished by injection, topical administration, and oral administration or by other methods alone or in combination with other known techniques.

As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In certain instances, the human is elderly. In other instances, the human is 65 years of age or older. Other examples of subjects include experimental animals such as mice, rats, dogs, cats, goats, sheep, pigs, and cows.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

The following examples are provided to better illustrate the claimed methods and compositions and are not to be interpreted as limiting the scope of the methods and compositions described herein. To the extent that specific materials are mentioned, it is merely for purposes of illustration and is not intended to limit the methods and compositions described herein. One skilled in the art may develop equivalent means or reactants without the exercise of inventive capacity and without departing from the scope of the methods and compositions described herein.

Example 1: Formulations

TABLE 2

Pilocarpine Oral Solution Formulation 1
Pilocarpine Oral Solution (1.0 mg/mL)

| Ingredients | % w/v | mg/ml | % w/v** | *IID Limit |
|---|---|---|---|---|
| Pilocarpine HCl | 0.1 | 1.000 | 0.09174 | NA |
| Hydroxyethylcellulose (Natrasol 250 HHX) | 0.2 | 2.000 | 0.18349 | 3 |
| Citric Acid, Anhydrous | 0.5 | 5.000 | 0.45872 | 0.75 |
| FD&C Red No. 40 | 0.0015 | 0.015 | 0.00138 | 0.05 |
| FD&C Blue No. 1 | 0.0005 | 0.005 | 0.00046 | 0.01 |
| Flavor Grape 59266/A | 0.04 | 0.400 | 0.03670 | 0.1 |
| Glycerin | 20.00 | 200.000 | 18.3486 | 22.2 |
| Propylene Glycol | 5.00 | 50.000 | 4.58716 | 20 |
| Poloxamer 407 | 0.5 | 5.000 | 0.45872 | 1 |
| Simethicone Emulsion | 0.05 | 0.500 | 0.04587 | 0.5 |
| Sodium Citrate, Dihydrate | 0.35 | 3.500 | 0.32110 | 1.58 |
| Sodium Benzoate | 0.15 | 1.500 | 0.13761 | 9.8 |
| Sucralose | 0.015 | 0.150 | 0.01376 | 1.1 |

TABLE 2-continued

Pilocarpine Oral Solution Formulation 1
Pilocarpine Oral Solution (1.0 mg/mL)

| Ingredients | % w/v | mg/ml | % w/v** | *IID Limit |
|---|---|---|---|---|
| Sorbitol Solution (70%) | 15.00 | 150.000 | 13.76147 | 0.6 |
| Purified Water | Q.S. | QS | 61.55321 | NA |

*Inactive Ingredient Database
**Adjusted for a specific gravity of 1.09

TABLE 3

Pilocarpine Oral Solution Formulation 2
Pilocarpine Oral Solution (1.0 mg/mL)

| Ingredients | % w/v | mg/ml | % w/v** | *IID Limit |
|---|---|---|---|---|
| Pilocarpine HCl | 0.1 | 1.000 | 0.09174 | NA |
| Hydroxyethylcellulose (Natrasol 250HHX) | 0.2 | 2.000 | 0.18349 | 3 |
| Citric Acid, Anhydrous | 0.5 | 5.000 | 0.45872 | 0.75 |
| FD&C Red No. 40 | 0.002 | 0.005 | 0.00138 | 0.05 |
| FD&C Blue No. 1 | 0.0006 | 0.005 | 0.00046 | 0.01 |
| Flavor Grape 59266/A | 0.04 | 0.400 | 0.03670 | 0.1 |
| Glycerin | 20.00 | 200.000 | 18.3482 | 22.2 |
| Propylene Glycol | 5 | 50.000 | 4.58716 | 20 |
| Poloxamer 407 | 0.5 | 5.000 | 0.45872 | 1 |
| Simethicone Emulsion | 0.1 | 0.500 | 0.04587 | 0.5 |
| Sodium Citrate, Dihydrate | 0.3 | 3.500 | 0.32110 | 1.58 |
| Sodium Benzoate | 0.15 | 1.500 | 0.13761 | 9.8 |
| Sucralose | 0.015 | 0.150 | 0.01376 | 1.1 |
| Purified Water | Q.S. | QS | 75.31467 | NA |

*Inactive Ingredient Database
**Adjusted for a specific gravity of 1.09

TABLE 4

Pilocarpine Oral Solution Formulation 3
Pilocarpine Oral Solution (1.0 mg/mL)

| Ingredients | % w/v | mg/ml | % w/v** | *IID Limit |
|---|---|---|---|---|
| Pilocarpine HCl | 0.1 | 1.000 | 0.09174 | NA |
| Hydroxyethylcellulose (Natrasol 250 HHX) | 0.2 | 2.000 | 0.18349 | 3 |
| Citric Acid, Anhydrous | 0.5 | 5.000 | 0.45872 | 0.75 |
| Flavor Grape 59266/A | 0.04 | 0.400 | 18.34862 | 0.1 |
| Glycerin | 20.00 | 200.000 | 4.58716 | 22.2 |
| Propylene Glycol | 5.00 | 50.000 | 0.45872 | 20 |
| Poloxamer 407 | 0.5 | 5.000 | 0.04587 | 1 |
| Simethicone Emulsion | 0.1 | 0.500 | 0.32110 | 0.5 |
| Sodium Citrate, Dihydrate | 0.35 | 3.500 | 0.13761 | 1.58 |
| Sodium Benzoate | 0.15 | 1.500 | 0.01376 | 9.8 |
| Sucralose | 0.015 | 0.150 | 0.03670 | 1.1 |
| Purified Water | Q.S. | QS | 75.31651 | NA |

*Inactive Ingredient Database
**Adjusted for a specific gravity of 1.09

TABLE 5

Pilocarpine Oral Solution Formulation 4
Pilocarpine Oral Solution (1.0 mg/mL)

| Ingredient | % w/v | mg/ml | % w/w** | *IID Limit |
|---|---|---|---|---|
| Pilocarpine HCl | 0.1000 | 1.000 | 0.09174 | NA |
| Hydroxyethylcellulose (Natrasol 250 HHX) | 0.15000 | 3.000 | 0.18349 | 3 |
| Citric Acid, Anhydrous, USP | 0.5000 | 5.000 | 0.45872 | 0.75 |

TABLE 5-continued

Pilocarpine Oral Solution Formulation 4
Pilocarpine Oral Solution (1.0 mg/mL)

| Ingredient | % w/v | mg/ml | % w/w** | *IID Limit |
|---|---|---|---|---|
| FD&C Red No. 40 | 0.0015 | 0.015 | 0.00138 | 0.05 |
| FD&C Blue No. 1 | 0.0005 | 0.005 | 0.00046 | 0.01 |
| Flavor Grape 59266/A | 0.0400 | 0.400 | 0.03670 | 0.1 |
| Glycerin, USP | 15.0000 | 150.000 | 18.34862 | 22.2 |
| Propylene Glycol, USP | 5.0000 | 50.000 | 4.58716 | 20 |
| Poloxamer 407 | 0.5000 | 5.000 | 0.45872 | 1 |
| Simethicone Emulsion | 0.0500 | 0.500 | 0.04587 | 0.5 |
| Sodium Citrate, Dihydrate | 0.3500 | 3.500 | 0.32110 | 1.58 |
| Sodium Benzoate, NF | 0.1500 | 1.500 | 0.13761 | 9.8 |
| Sucralose, NF | 0.0150 | 0.150 | 0.01376 | 1.1 |
| Sorbitol Solution 70% | 15.0000 | 150.000 | 13.76147 | 0.6 |
| Purified Water, USP | QS | QS | 61.55321 | NA |

*Inactive Ingredient Database
**Adjusted for a specific gravity of 1.09

TABLE 6

Pilocarpine Oral Solution Formulation 5
Pilocarpine Oral Solution (1.0 mg/mL)

| Ingredients | % w/v | mg/ml | % w/v** | *IID Limit |
|---|---|---|---|---|
| Pilocarpine HCl | 0.1 | 1.000 | 0.09174 | NA |
| Hydroxyethylcellulose (Natrasol 250 HHX) | 0.15 | 3.000 | 0.18349 | 3 |
| Citric Acid, Anhydrous | 0.5 | 5.000 | 0.45872 | 0.75 |
| FD&C Red No. 40 | 0.002 | 0.005 | 0.00138 | 0.05 |
| FD&C Blue No. 1 | 0.0006 | 0.005 | 0.00046 | 0.01 |
| Flavor Grape 59266/A | 0.04 | 0.400 | 0.03670 | 0.1 |
| Glycerin | 15.00 | 150.000 | 18.3482 | 22.2 |
| Propylene Glycol | 5 | 50.000 | 4.58716 | 20 |
| Poloxamer 407 | 0.5 | 5.000 | 0.45872 | 1 |
| Simethicone Emulsion | 0.05 | 0.500 | 0.04587 | 0.5 |
| Sodium Citrate, Dihydrate | 0.35 | 3.500 | 0.32110 | 1.58 |
| Sodium Benzoate | 0.15 | 1.500 | 0.13761 | 9.8 |
| Sucralose | 0.015 | 0.150 | 0.01376 | 1.1 |
| Purified Water | Q.S. | QS | 75.31467 | NA |

*Inactive Ingredient Database
**Adjusted for a specific gravity of 1.09

TABLE 7

Pilocarpine Oral Solution Formulation 6
Pilocarpine Oral Solution (1.0 mg/mL)

| Ingredients | % w/v | mg/ml | % w/v** | *IID Limit |
|---|---|---|---|---|
| Pilocarpine HCl | 0.1 | 1.000 | 0.09174 | NA |
| Hydroxyethylcellulose (Natrasol 250HHX) | 0.15 | 3.000 | 0.18349 | 3 |
| Citric Acid, Anhydrous | 0.5 | 5.000 | 0.45872 | 0.75 |
| Flavor Grape 59266/A | 0.04 | 0.400 | 18.34862 | 0.1 |
| Glycerin | 20.00 | 200.000 | 4.58716 | 22.2 |
| Propylene Glycol | 5.00 | 50.000 | 0.45872 | 20 |
| Poloxamer 407 | 0.5 | 5.000 | 0.04587 | 1 |
| Simethicone Emulsion | 0.05 | 0.500 | 0.32110 | 0.5 |
| Sodium Citrate, Dihydrate | 0.35 | 3.500 | 0.13761 | 1.58 |
| Sodium Benzoate | 0.15 | 1.500 | 0.01376 | 9.8 |
| Sucralose | 0.015 | 0.150 | 0.03670 | 1.1 |
| Purified Water | Q.S. | QS | 75.31651 | NA |

Tables 2 through 7 show exemplary pilocarpine oral solution formulation including the ingredients, percent weight per volume, and inactive ingredient database (IID) limit.

In some embodiments, the formulation includes 0.5% w/v of citric acid, anhydrous, 0.0006% w/v of FD&C Blue No. 1, 0.002% w/v of FD&C Red No. 40, 0.04% w/v of Flavor Grape 59266/A, 15% w/v of glycerin, 0.1% w/v of hydroxyethylcellulose (Natrasol 250HHX), 0.1% w/v of pilocarpine HCl, 0.5% w/v of poloxamer 407, 5% w/v of propylene glycol, 0.1% w/v of simethicone emulsion, 0.3% w/v of sodium citrate, dihydrate, 0.15% w/v of sodium benzoate, 15% w/v of sorbitol solution (70%), 0.015% w/v of sucralose, and purified water, as seen in Table 2.

In other embodiments, the formulation includes 0.5% w/v of citric acid, anhydrous, 0.0006% w/v of FD&C Blue No. 1, 0.0015% w/v of FD&C Red No. 40, 0.04% w/v of Flavor Grape 59266/A, 20% w/v of glycerin, 0.1% w/v of hydroxyethylcellulose (Natrasol 250HHX), 0.1% w/v of pilocarpine HCl, 0.5% w/v of poloxamer 407, 5% w/v of propylene glycol, 0.01% w/v of simethicone emulsion, 0.3% w/v of sodium citrate dihydrate, 0.15% w/v of sodium benzoate, 15% w/v of sorbitol solution (70%), 0.015% w/v of sucralose, and purified water, as seen in Table 3.

Example 2: Stability

Pilocarpine has been shown to be unstable at room temperature in solution (Fawcett et al.). Pilocarpine mouth rinse solutions and eye drops need to be stored in cool, dry places, and must be disposed of after limited times (e.g., GLANDOMED® mouth rinse solution). These forms of pilocarpine solution sensitive to high temperatures and unstable. The product information from various suppliers of pilocarpine state that pilocarpine should be stored at room temperature or at refrigerated temperature to maintain stability, for only 30-90 days.

Surprisingly, a stable oral pilocarpine solution has been developed according to the invention. The pilocarpine solution was formulated and assayed for pilocarpine levels. Stability of the claimed formulation was tested at room temperature, 30° C., and 40° C. and assayed for the pilocarpine. Results for 7.5 months can be found in Table 8 below.

TABLE 8

Stability Results of Pilocarpine HCl Oral Solution, 1.0 mg/mL
Stability Results of Pilocarpine Solution

| Sample Description | % Assay result |
|---|---|
| 111015A, 7.5 mo., RT | 95.6 |
| 111015A, 7.5 mo., 30 C. | 94.9 |
| 111015A, 7.5 mo., 40 C. | 93.8 |
| 111015A, 7.5 mo., 5 C. | 97.2 |

Table 9 shows further stability data up through 6 months under accelerated conditions. The fact that the oral solution was stable after 6 months at an accelerated temperature (which is predictive of assay conditions for 48 months at room temperature) was quite surprising. The percent impurities were only tested for the 6 month data in Table 6. The results were as follows at 25° C./60% RH: isopilocarpine, placebo interference, pilocarpic acid, none detected, isopilocarpic acid, none detected, and unspecified purities consisted of RRT 0.51/0.42, RRT 0.87/<0.05, RRT 1.53/<0.05, RRT 1.67/<0.05, RRT 1.68/<0.05, RRT 1.91/<0.05, RRT 2.02/<0.05, RRT 2.27/<0.05, RRT 2.28/<0.05, RRT 7.84/<0.05, and RRT 7.86/<0.05, totaling 0.42. The results at 6 months were as follows at 30° C./65% RH: isopilocarpine, placebo interference, pilocarpic acid, none detected, isopilocarpic acid, none detected, and unspecified purities consisted of RRT 0.51/0.47, RRT 0.84/<0.05, RRT 0.87/<0.05, RRT 1.53/<0.05, RRT 1.67/<0.05, RRT 1.91/<0.05, RRT 2.02/<0.05, RRT 2.28/<0.05, RRT 2.43/<0.05, RRT 7.83/<0.05, and RRT 7.85/<0.05, totaling 0.47. The results at 6 months were as follows at 40° C./75% RH: isopilocarpine, placebo interference, pilocarpic acid, none detected, isopilocarpic acid, none detected, and unspecified purities consisted of RRT 0.51/0.55, RRT 0.67/0.12, RRT 0.83/<0.05, RRT 0.87/<0.05, RRT 1.10/0.08, RRT 1.46/<0.05, RRT 1.53/<0.05, RRT 1.68/<0.05, RRT 1.71/<0.05, RRT 1.91/<0.05, RRT 2.03/<0.05, RRT 2.27/<0.05, RRT 2.431<0.05, RRT 4.661<0.05, RRT 4.711<0.05, RRT 7.811<0.05, and RRT 7.821<0.05, totaling 0.75.

TABLE 9

Stability Results of Pilocarpine HCl Oral Solution, 1.0 mg/mL,
under room temperature and accelerated conditions
R & D Stability Report for Pilocarpine HCl Oral Solution, 1.0 mg/mL
Product: Pilocarpine HCl Oral
Lot #: 050516A  Packaging: White PET bottle

| Test/Method | Storage Temperature | Initial | 1 Month | 2 Months | 3 Months | 6 Months |
|---|---|---|---|---|---|---|
| Assay by HPLC | 25° C./60% RH | 99.1% | 97.4% | 97.5% | 96.5% | 96.1% |
| Impurities | | NT | NT | NT | NT | 0.42 |
| Sodium Benzoate Assay | | NT | NT | NT | NT | 99.7% |
| Assay by HPLC | 30° C./65% RH | 99.1% | 97.5% | 96.0% | 96.0% | 95.5% |
| Impurities | | NT | NT | NT | NT | 0.47 |
| Sodium Benzoate Assay | | NT | NT | NT | NT | 99.8% |
| Assay by HPLC | 40° C./75% RH | 99.1% | 96.0% | 95.3% | 94.2% | 94.7% |
| Impurities | | NT | NT | NT | NT | 0.75 |
| Sodium Benzoate Assay | | NT | NT | NT | NT | 99.3% |

NT = Not Tested

Table 10 shows additional stability data up through two months. The data presented herein show that an oral pilocarpine solution can remain stable with minimal degradants and thus have a long shelf life consistent with commercial formulations.

TABLE 10

Stability Results of Pilocarpine HCl Oral Solution, 1.0 mg/mL, under room
temperature and accelerated conditions
R & D Stability Report for Pilocarpine HCl Oral Solution, 1.0 mg/mL
Product: Pilocarpine HCl Oral
Lot #: 092816A  Packaging: White PET bottle

| Test/Method | Storage Temperature | Initial | 1 Month | 2 Months |
|---|---|---|---|---|
| Assay by HPLC Impurities | 25° C./60% RH | 100.9% Isopilocarpine: placebo interference | 101.1% placebo interference | 99.2% placebo interference |

TABLE 10-continued

Stability Results of Pilocarpine HCl Oral Solution, 1.0 mg/mL, under room
temperature and accelerated conditions
R & D Stability Report for Pilocarpine HCl Oral Solution, 1.0 mg/mL
Product: Pilocarpine HCl Oral
Lot #: 092816A                              Packaging: White PET bottle

| Test/Method | Storage Temperature | Initial | 1 Month | 2 Months |
|---|---|---|---|---|
| | | Pilocarpic Acid: None detected | None detected | None detected |
| | | Isopilocarpic Acid: None detected | None detected | None detected |
| | | Unspecified impurities: RRT 1.53/0.05 | RRT 1.54/0.05 | RRT 0.51/0.27 |
| | | RRT 1.90/0.05 | RRT 1.93/0.05 | RRT 1.53/0.05 |
| | | RRT 2.02/0.05 | RRT 2.04/0.05 | RRT 1.90/0.05 |
| | | | | RRT 2.02/0.05 |
| | | | | RRT 2.73/0.05 |
| | | | | RRT 3.68/0.05 |
| | | | | RRT 3.69/0.05 |
| | | | | RRT 7.87/0.05 |
| | | | | RRT 7.89/0.05 |
| | | | | Total: 0.27 |
| Sodium Benzoate Assay | | NT | NT | 100.8% |
| Assay by HPLC Impurities | 30° C./65% RH | 100.9% | 100.5% | 98.6% |
| | Isopilocarpine: | placebo interference | placebo interference | placebo interference |
| | Pilocamic Acid: | None detected | None detected | None detected |
| | Isopilocarpic Acid: | None detected | None detected | None detected |
| | Unspecified impurities: | RRT 1.53/0.05 | RRT 1.54/0.05 | RRT 0.51/0.34 |
| | | RRT 1.90/0.05 | RRT 1.93/0.05 | RRT 1.53/0.05 |
| | | RRT 2.02/0.05 | RRT 2.04/0.05 | RRT 1.90/0.05 |
| | | | | RRT 2.02/0.05 |
| | | | | RRT 2.73/0.05 |
| | | | | RRT 2.74/0.05 |
| | | | | RRT 3.68/0.05 |
| | | | | RRT 7.87/0.05 |
| | | | | Total: 0.34 |
| Sodium Benzoate Assay | | NT | NT | 100.7% |
| Assay by HPLC Impurities | 40° C./75% RH | 100.9% | 99.0% | 96.8% |
| | Isopilocarpine: | placebo interference | placebo interference | placebo interference |
| | Pilocamic Acid: | None detected | None detected | None detected |
| | Isopilocarpic Acid: | None detected | None detected | None detected |
| | Unspecified impurities: | RRT 1.53/0.05 | RRT 1.54/0.05 | RRT 0.51/0.34 |
| | | RRT 1.90/0.05 | RRT 1.93/0.05 | RRT 0.87/0.05 |
| | | RRT 2.02/0.05 | RRT 2.04/0.05 | RRT 1.53/0.05 |
| | | | | RRT 1.91/0.05 |
| | | | | RRT 2.02/0.05 |
| | | | | RRT 2.73/0.05 |
| | | | | RRT 3.67/0.05 |
| | | | | RRT 3.69/0.05 |
| | | | | RRT 6.26/0.05 |
| | | | | RRT 7.86/0.05 |
| | | | | RRT 7.89/0.05 |
| | | | | Total: 0.46 |
| Sodium Benzoate Assay | | NT | NT | 99.9% |

NT = Not Tested

The results from Tables 8, 9, and 10 show pilocarpine is stable compared to the initial raw API used and under all conditions after up to 6 months. These results show that the pilocarpine solution (Pilocarpine HCl Oral Solution, 1.0 mg/mL) of the invention is stable, even at high temperatures with high relative humidity. The results were calculated on an as is basis. The pilocarpine solution in Table 6 and Table 7 were packaged in a white PET bottle and assayed by HPLC cUSP. The percent values are relative to the label claims, 1 mg/mL.

Example 3: Pilocarpine Dissolution Study

The purpose of this study was to evaluate and compare the dissolution behavior of three Pilocarpine dosage forms. Pilocarpine Hydrochloride Oral Solution 1 mg/mL was compared to reference dosage forms Pilocarpine Hydrochloride 7.5 mg and 5 mg Tablets. Dissolution testing was performed according to the parameters outlined within the USP monograph for Pilocarpine Hydrochloride Tablets.

The dissolution behavior of each of the three aforementioned dosage forms was evaluated under the following conditions prescribed under the 2016 USP monograph for Pilocarpine HCl Tablets. Multiple sampling points were performed to construct a profile, including the 45 minute time point included in the monograph. USP Apparatus 2 (Paddles) were used at 50 RPM. The dissolution media was 0.1 N HCl (500 mL, 37° C.±0.5° C.)). Sample were taken at 5, 10, 15, 20, 30, 45, and 60 minutes for profile comparison. High performance liquid chromatography (HPLC was used with the following parameters: UV at 215 nm, 4.6 mm×15 cm L1 (C18), 1 mL/minute Methanol:Buffer 3:17). The sample size was 6.

Materials

The analytical samples and materials used in the studies are listed in Table 11.

TABLE 11

Samples and Reference Materials

| Description | Manufacture/Source | Lot #/Reference # | Storage Condition/Grade |
|---|---|---|---|
| Pilocarpine HCl RS, USP | USP | R033R0 | 2-8° C./99.7% |
| Pilocarpine HCl Liquid | Romeg, Inc. | 092816A | 20-25° C. |
| Pilocarpine HCl Tablets, 5 mg | Actavis | VDHG | 20-25° C. |
| Pilocarpine HCl Tablets, 7.5 mg | Actavis | WCNM | 20-25° C. |
| Water | Deionized, ≥18 MΩ/cm In house | N/A | N/A |
| Hydrochloric Acid (HCl) | Spectrum | 2FD0303 | Concentrated |
| Phosphoric Acid | Merck | 56035617 | 85% |
| Triethylamine | Spectrum | 2EE0202 | 99% |
| Methanol | Spectrum | 16060430 | HPLC |
| Sodium Hydroxide | JT Baker | 0000085138 | 50% |
| Filters, 45 μm Polyethylene membrane | QLA | N/A | N/A |

Dissolution Study

Sample Preparation

For the 5 mg and 7.5 mg Pilocarpine HCl tablets, samples were tested as is. For the Pilocarpine Hydrochloride Oral Solution 1 mg/mL, an aliquot equivalent to 7.5 mg (7.5 mL) was introduced into each dissolution vessel for equivalency to the highest tablet label claim.

Dissolution Analysis

Experimental Approach

A 6 unit dissolution test was performed for each of three dosage forms using 0.1 N HCl as dissolution medium. For each dissolution study, the dissolution medium was prepared and degassed according to USP guidelines (filtration under vacuum at 41° C.). 500 mL of media was added to each dissolution vessel and equilibrated to 37° C.±0.5° C. A tablet or 7.5 mL aliquot of solution was introduced into each of 6 dissolution vessels. USP Apparatus 2 paddles were operated at 50 RPM. At the specified sampling times of 5, 10, 15, 20, 30, 45 and 60 minutes, 2.0 mL aliquots were withdrawn using a syringe and cannula equipped with a 45 μm polyethylene filter. System suitability was established using standard prepared in dissolution media (0.1 N HCl). Quantitation was performed using overlapping bracketing standard injections. For calculation, the total dissolution vessel volume was normalized at 500 mL, and did not account for the 7.5 mL addition of liquid sample for the Pilocarpine Oral Solution.

Results

Figure 2:
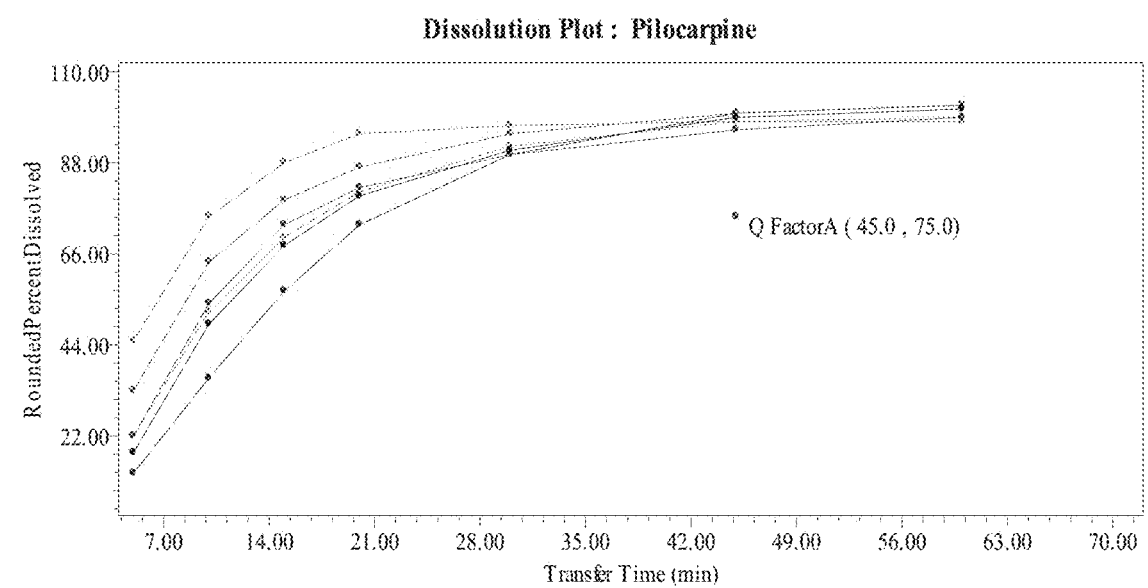
FIG. 2 depicts a dissolution plot for pilocarpine hydrochloride tablets, 7.5 mg corresponding to the data presented in Table 10.
Figure 3:
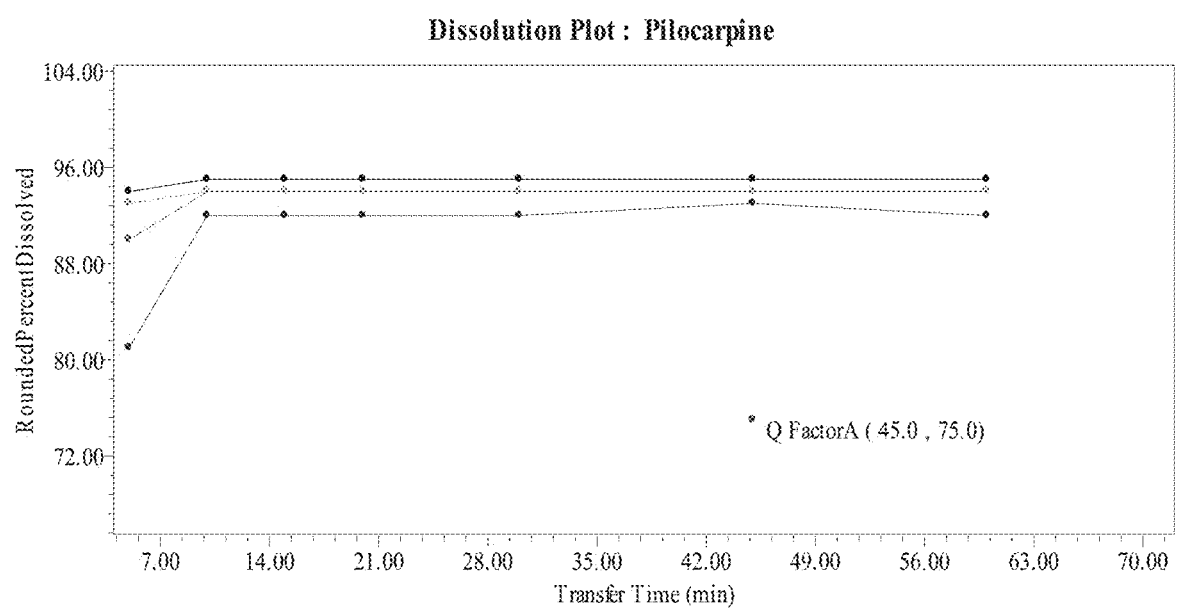
FIG. 3 depicts a dissolution plot for pilocarpine hydrochloride solution, 1 mg/mL corresponding to the data presented in Table 11.

The dissolution results obtained for each of three dosage forms are included in Tables 12-14. Dissolution plots are included as FIGS. 1-3.

TABLE 12

Dissolution for Pilocarpine Hydrochloride Tablets, 5.0 mg

| | % Dissolved | | | | | | |
|---|---|---|---|---|---|---|---|
| Vessel | 5 min | 10 min | 15 min | 20 min | 30 min | 45 min | 60 min |
| 1 | 47 | 71 | 86 | 92 | 97 | 99 | 99 |
| 2 | 35 | 69 | 86 | 94 | 98 | 100 | 100 |
| 3 | 42 | 73 | 86 | 93 | 99 | 101 | 101 |
| 4 | 26 | 59 | 77 | 87 | 96 | 100 | 100 |
| 5 | 37 | 68 | 84 | 92 | 97 | 100 | 101 |
| 6 | 29 | 59 | 80 | 90 | 98 | 100 | 101 |
| Mean (6) | 36 | 67 | 83 | 91 | 98 | 100 | 100 |
| % Relative standard deviation (RSD) | 21.8 | 9.1 | 4.6 | 2.7 | 1.1 | 0.6 | 0.8 |
| Max | 47 | 73 | 86 | 94 | 99 | 101 | 101 |
| Min | 26 | 59 | 83 | 87 | 96 | 99 | 99 |

TABLE 13

Dissolution for Pilocarpine Hydrochloride Tablets, 7.5 mg

| | % Dissolved | | | | | | |
|---|---|---|---|---|---|---|---|
| Vessel | 5 min | 10 min | 15 min | 20 min | 30 min | 45 min | 60 min |
| 1 | 18 | 49 | 68 | 80 | 91 | 99 | 101 |
| 2 | 22 | 54 | 73 | 82 | 90 | 96 | 99 |
| 3 | 45 | 75 | 88 | 95 | 97 | 98 | 98 |
| 4 | 22 | 52 | 70 | 81 | 92 | 98 | 99 |
| 5 | 33 | 64 | 79 | 87 | 95 | 100 | 102 |
| 6 | 13 | 36 | 57 | 73 | 90 | 100 | 102 |
| Mean (6) | 26 | 55 | 73 | 83 | 93 | 99 | 100 |
| % RSD | 45.5 | 24.2 | 14.5 | 8.9 | 3.1 | 1.5 | 1.7 |
| Max | 45 | 75 | 88 | 95 | 97 | 100 | 102 |
| Min | 13 | 36 | 57 | 73 | 90 | 96 | 98 |

TABLE 14

Dissolution for Pilocarpine Hydrochloride Solution, 1 mg/mL

| | % Dissolved | | | | | | |
|---|---|---|---|---|---|---|---|
| Vessel | 5 min | 10 min | 15 min | 20 min | 30 min | 45 min | 60 min |
| 1 | 94 | 95 | 95 | 95 | 95 | 95 | 95 |
| 2 | 94 | 95 | 95 | 95 | 95 | 95 | 95 |
| 3 | 94 | 95 | 95 | 95 | 95 | 95 | 95 |
| 4 | 93 | 94 | 94 | 94 | 94 | 94 | 94 |
| 5 | 90 | 94 | 94 | 94 | 94 | 94 | 94 |
| 6 | 81 | 92 | 94 | 92 | 92 | 93 | 92 |
| Mean (6) | 91 | 94 | 94 | 94 | 94 | 94 | 94 |

TABLE 14-continued

Dissolution for Pilocarpine Hydrochloride Solution, 1 mg/mL

| | % Dissolved | | | | | | |
|---|---|---|---|---|---|---|---|
| Vessel | 5 min | 10 min | 15 min | 20 min | 30 min | 45 min | 60 min |
| % RSD | 5.6 | 1.2 | 1.2 | 1.2 | 1.2 | 0.9 | 1.2 |
| Max | 94 | 95 | 95 | 95 | 95 | 95 | 95 |
| Min | 81 | 92 | 92 | 92 | 92 | 93 | 92 |

Conclusion

For each of the tablet dosage forms (5 mg and 7.5 mg), Stage 1 acceptance criteria were met per the requirements of USP <711> Dissolution, with no individual unit less than Q+5% (Q=75%) dissolved at 45 minutes. Per the requirements of current Biopharmaceutics Classification System (BCS) guidance, the oral solution would be expected to qualify as "very rapidly dissolving" in 0.1 N HCl, with 85 percent or more of the labeled amount of the drug substance dissolved within 15 minutes. It was surprising that the oral solution rapidly dissolves at a rate comparable to both the 5 mg and 7.5 mg pilocarpine tablets.

Example 4: Caco-2 Permeability of Pilocarpine

Purpose

The objective of this study was to evaluate the bidirectional Caco-2 permeability of three formulations of test article Pilocarpine at three pH levels (pH 5.7, 6.5, 7.4) using calibration curve quantitation.

Study Conditions

This study was performed under non-GLP conditions. All work was performed with appropriate local health regulations and ethical approval.

Experimental Design

Mass Spectrometry Method Development

The analyte signal was optimized for each compound by electro-spray positive or negative ionization mode (ESI). An MS2 scan or an SIM scan was used to optimize the fragmenter voltage, a product ion analysis was used to identify the best fragment for analysis, and the collision energy was optimized using a product ion (or MRM) scan. An ionization ranking is assigned to each analyte, indicating the compound's ease of ionization. Table 15 below details the test articles used in the Caco-2 permeability study.

TABLE 15

Test Articles

| Test Article | Parent MW (Free Base) | Amount | Physical Form |
|---|---|---|---|
| Pilocarpine HCl liquid (Romeg) | 208.257 | 1 mg/ml | |
| Pilocarpine HCl 5.0 mg (Salagen) | 208.257 | 5 mg | tablet |
| Pilocarpine HCl 7.5 mg (Salagen) | 208.257 | 7.5 mg | tablet |

Sample Analysis

Samples were analyzed by LC/MS/MS using an Waters Xevo TQ mass spectrometer coupled with an Acuity HPLC and a CTC PAL chilled autosampler, all controlled by MassLynx software (Waters). After separation on a C18 reverse phase (Waters Acquity HSS T3 2.1×50 mm 1.8 µM) using an acetonitrile-water gradient system, peaks were analyzed by mass spectrometry (MS) using ESI ionization in MRM mode.

Tables 16-17 show the HPLC gradients used and the experiment conditions of the Caco-2 permeability test, respectively. The reference compounds used were ranitidine (non-permeable), talinolol (semi-permeable), and metoprolol (highly permeable).

TABLE 16

HPLC Gradient

| Time (mm) | Flow rate (uL/min) | % A Mobile Phase | % B Mobile Phase |
|---|---|---|---|
| 0.05 | 0.6 | 99.9 | 0.1 |
| 1.0 | 0.6 | 5 | 95 |
| 1.40 | 0.6 | 5 | 95 |
| 1.41 | 0.6 | 99.9 | 0.1 |
| 1.8 | 0.6 | 99.9 | 0.1 |

Solution A: H$_2$O with 0.1% Formic acid;
Solution B: Acetonitrile with 0.1% Formic acid

TABLE 17

Experimental Conditions: Caco-2 Permeability

| Test Article | Test Conc. | Assay Time | Transport Direction | Reference Compounds | Analytical Method |
|---|---|---|---|---|---|
| Pilocarpine HCl liquid Pilocarpine HCl 5.0 mg Pilocarpine HCl 7.5 mg | 10 µM | 2 hours | A→B B→A | Ranitidine Talinolol Metoprolol | LC-MS/MS |

Caco-2 Permeability Experimental Procedure:

Caco-2 cells grown in tissue culture flasks were trypsinized, suspended in medium, and the suspensions were applied to wells of a Millipore 96 well plate. The cells were allowed to grow and differentiate for three weeks, feeding at 2-day intervals.

For Apical to Basolateral (A→B) permeability, the test article was added to the apical (A) side and amount of permeation was determined on the basolateral (B) side; for Basolateral to Apical (B→A) permeability, the test article was added to the B side and the amount of permeation was determined on the A side. The A-side buffer contained 100 µM Lucifer yellow dye, in Transport Buffer (1.98 g/L glucose in 10 mM HEPES, 1× Hank's Balanced Salt Solution) pH-5.7, pH-6.5 and pH-7.4, the B-side buffer was Transport Buffer always at pH 7.4. Caco-2 cells were incubated with test articles in these buffers for 2 hours, and at the end of the assay, donor and receiver side solution samples were collected, quenched by 100% methanol containing an internal standard and centrifuged at 5000 rpm for 10 minutes at 4° C. Following centrifugation, the supernatant for donor and receiver side samples were analyzed by LC-MS/MS.

Data Analysis:

Data is expressed as permeability ($P_{app}$):

$$P_{app} = \frac{dQ/dt}{C_0 A}.$$

dQ/dt is rate of permeation, $C_0$ is initial concentration of test article, and A is the area of monolayer.

In bidirectional permeability studies, Efflux Ratio ($R_e$) is also calculated:

$$R_e = \frac{P_{app}(B \to A)}{P_{app}(A \to B)}.$$

$R_e > 2$ indicates a potential substrate for P-gp or other active efflux transporters. The donor, dosing and receiver side sample concentrations were calculated based on the calibration curve prepared in buffer matrix in the range of 1-20,000 nM.

Calibration Curve of Pilocarpine in Buffer and Tablet Extraction Efficiency

Figure 4:
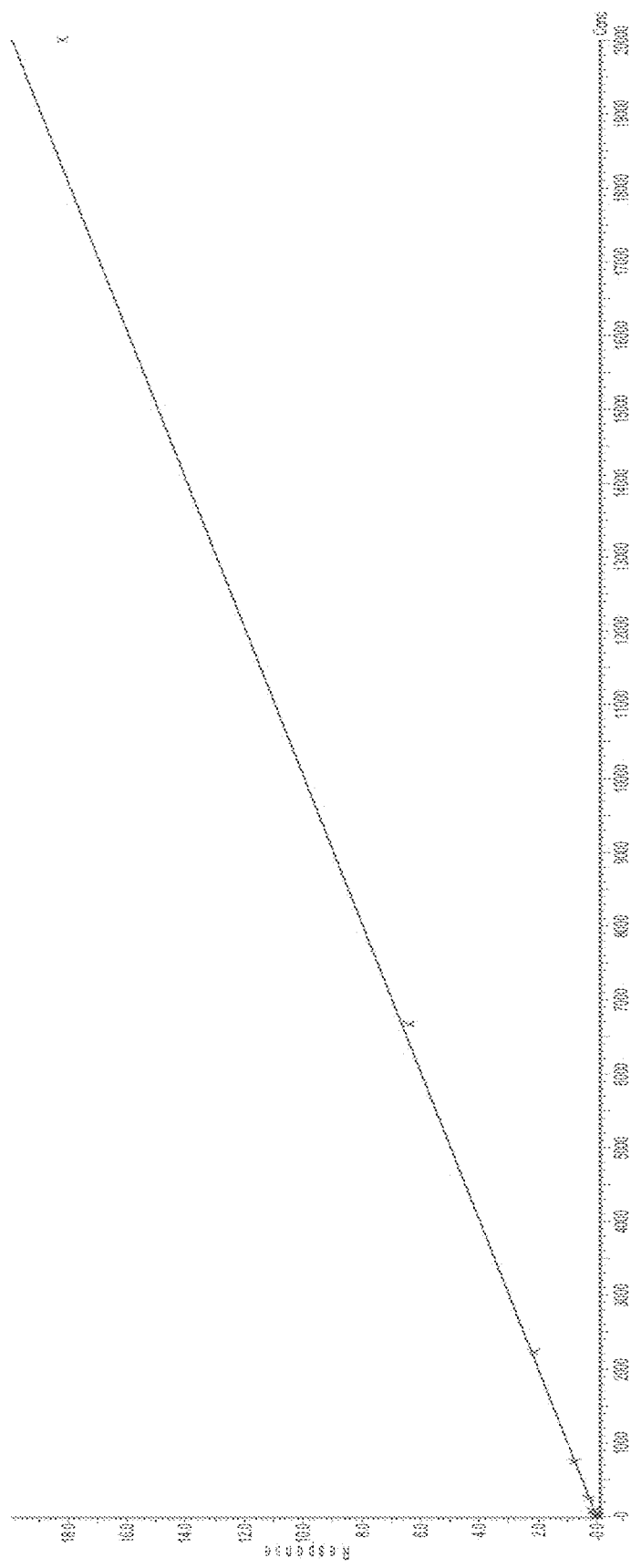
FIG. 4 shows a graph depicting the calibration curve of pilocarpine in buffer and tablet extraction efficiency.

Linear fit calibration curve (FIG. 4) was used, with a 1/×2 weighting factor applied to the data points. In buffer, the LLOQ (lower limit of quantification) and ULOQ (upper limit of quantification) was established as 1.0 nM and 20,000 nM respectively. Table 16 shows the extraction efficiency of three samples for each of the 5.0 mg and the 7.5 mg tablets. Table 19 shows general information regarding the pilocarpine HCl tested.

TABLE 18

Extraction Efficiency.
Extraction Efficiency:

|  | 5 mg tablet (nM) | 5 mg tablet (uM) | % relative to 10 uM (expected) |
|---|---|---|---|
| sample-1 | 8749 | 8.75 | 87.5% |
| sample-2 | 8401 | 8.40 | 84.0% |
| sample-3 | 7936 | 7.94 | 79.4% |

TABLE 18-continued

Extraction Efficiency.
Extraction Efficiency:

|  | 7.5 mg tablet (nM) | 7.5 mg tablet (uM) | % relative to 10 uM (expected) |
|---|---|---|---|
| sample-1 | 8919 | 8.92 | 89.2% |
| sample-2 | 8407 | 8.41 | 84.1% |
| sample-3 | 8024 | 8.02 | 80.2% |

Note:
All Papp rate coefficients were calculated based on the above-listed actual concentrations in dosing samples (not the nominal, expected concentration)

Results

TABLE 19

Analytical Method Development: MS/MS

| Test Article | MW | ESI Polarization | Precursor m/z | Product m/z | Ionization Classification |
|---|---|---|---|---|---|
| Pilocarpine HCl | 208.257 | Positive | 209.069 | 95.967 | 1 |

Ionization Classification:
1 = Highly ionizable;
2 = Moderately ionizable;
3 = Poorly ionizable
m/2z: mass-to-charge ratio of analyte (double charged)

TABLE 20

Data Summary: Caco-2 Permeability

| Test Article | pH (A/B) | Mean A → B Papp $10^{-6}$ cm/s$^{-1}$ | Mean B → A Papp $10^{-1}$ cm/s$^{-1}$ | Efflux Ratio | Comments |
|---|---|---|---|---|---|
| Pilocarpine HCl liquid | 5.7/7.4 | 5.82 | 23.7 | 4.07 |  |
| Pilocarpine HCl 5.0 mg | 5.7/7.4 | 6.58 | 24.4 | 3.70 |  |
| Pilocarpine HCl 7.5mg | 5.7/7.4 | 6.87 | 25.1 | 3.64 |  |
| Pilocarpine HCl liquid | 6.5/7.4 | 11.1 | 24.4 | 2.18 |  |
| Pilocarpine HCl 5.0 mg | 6.5/7.4 | 11.7 | 26.2 | 2.26 |  |
| Pilocarpine HCl 7.5 mg | 6.5/7.4 | 11.5 | 22.8 | 1.98 |  |
| Pilocarpine HCl liquid | 7.4/7.4 | 18.9 | 22.1 | 1.19 | High permeability |
| Pilocarpine HCl 5.0 mg | 7.4/7.4 | 22.1 | 21.9 | 0.998 | High permeability |
| Pilocarpine HCl 7.5 mg | 7.4/7.4 | 23.1 | 20.2 | 0.869 | High permeability |
| Metoprolol | 6.5/7.4 | 19.4 | 42.7 | 2.22 | High permeability BCS control |
| Ranitidine | 6.5/7.4 | 0.585 | 3.13 | 5.41 | Low permeability control |
| Talinolol | 6.5/7.4 | 0.409 | 11.9 | 56.4 | P-gp Efflux control |

Papp: apparent permeability rate coefficient
Efflux Ratio: Papp (B → A)/Papp (A → B)

TABLE 21

Individual Data of Replicates: Caco-2 Permeability

| Test Article | PH (A/B) | Transport Direction | Parameter | First Rep | Second Rep | Third Rep | Mean |
|---|---|---|---|---|---|---|---|
| Pilocarpine HCl liquid | 5.7/7.4 | A → B | Papp | 5.93 | 5.64 | 5.90 | 5.82 |
|  |  | A → B | Recovery | 35.4% | 38.8% | 37.6% | 37.2% |
|  |  | B → A | Papp | 22.4 | 22.4 | 26.4 | 23.7 |
|  |  | B → A | Recovery | 79.5% | 77.8% | 84.3% | 80.5% |
|  |  | (B → A)/(A → B) | Efflux Ratio | 3.77 | 3.97 | 4.47 | 4.07 |

TABLE 21-continued

Individual Data of Replicates: Caco-2 Permeability

| Test Article | PH (A/B) | Transport Direction | Parameter | First Rep | Second Rep | Third Rep | Mean |
|---|---|---|---|---|---|---|---|
| Pilocarpine HCl 5.0 mg | 5.7/7.4 | A → B | Papp | 6.48 | 6.53 | 6.73 | 6.58 |
| | | A → B | Recovery | 40.0% | 43.8% | 50.7% | 44.8% |
| | | B → A | Papp | 21.3 | 23.6 | 28.3 | 24.4 |
| | | B → A | Recovery | 79.8% | 74.6% | 98.3% | 84.3% |
| | | (B → A)/(A → B) | Efflux Ratio | 3.29 | 3.61 | 4.21 | 3.70 |
| Pilocarpine HCl 7.5 mg | 5.7/7.4 | A → B | Papp | 6.81 | 6.72 | 7.09 | 6.87 |
| | | A → B | Recovery | 42.1% | 43.0% | 39.6% | 41.6% |
| | | B → A | Papp | 23.7 | 22.9 | 28.6 | 25.1 |
| | | B → A | Recovery | 82.3% | 78.7% | 94.4% | 85.2% |
| | | (B → A)/(A → B) | Efflux Ratio | 3.47 | 3.40 | 4.04 | 3.64 |
| Pilocarpine HCl liquid | 6.5/7.4 | A → B | Papp | 10.7 | 11.1 | 11.7 | 11.1 |
| | | A → B | Recovery | 48.5% | 56.1% | 50.1% | 51.6% |
| | | B → A | Papp | 21.6 | 22.9 | 28.6 | 24.4 |
| | | B → A | Recovery | 71.9% | 76.6% | 82.4% | 77.0% |
| | | (B → A)/(A → B) | Efflux Ratio | 2.02 | 2.07 | 2.45 | 2.18 |
| Pilocarpine HCl 5.0 mg | 6.5/7.4 | A → B | Papp | 11.3 | 12.5 | 11.2 | 11.7 |
| | | A → B | Recovery | 47.5% | 51.4% | 50.8% | 49.9% |
| | | B → A | Papp | 26.9 | 22.1 | 29.6 | 26.2 |
| | | B → A | Recovery | 90.5% | 82.0% | 95.1% | 89.2% |
| | | (B → A)/(A → B) | Efflux Ratio | 2.37 | 1.77 | 2.64 | 2.26 |
| Pilocarpine HCl 7.5 mg | 6.5/7.4 | A → B | Papp | 11.8 | 11.7 | 11.2 | 11.5 |
| | | A → B | Recovery | 54.1% | 52.1% | 48.6% | 51.6% |
| | | B → A | Papp | 21.4 | 21.0 | 26.0 | 22.8 |
| | | B → A | Recovery | 83.9% | 77.9% | 87.3% | 83.0% |
| | | (B → A)/(A → B) | Efflux Ratio | 1.81 | 1.80 | 2.33 | 1.98 |
| Pilocarpine HCl liquid | 7.4/7.4 | A → B | Papp | 17.6 | 21.1 | 18.0 | 18.9 |
| | | A → B | Recovery | 48.2% | 58.4% | 50.1% | 52.3% |
| | | B → A | Papp | 23.2 | 19.2 | 23.9 | 22.1 |
| | | B → A | Recovery | 81.8% | 78.6% | 88.2% | 82.9% |
| | | (B → A)/(A → B) | Efflux Ratio | 1.32 | 0.912 | 1.33 | 1.19 |
| Pilocarpine HCl 5.0 mg | 7.4/7.4 | A → B | Papp | 21.4 | 24.7 | 20.3 | 22.1 |
| | | A → B | Recovery | 62.6% | 64.6% | 53.1% | 60.1% |
| | | B → A | Papp | 20.7 | 22.1 | 23.1 | 21.9 |
| | | B → A | Recovery | 77.8% | 83.5% | 83.9% | 81.7% |
| | | (B → A)/(A → B) | Efflux Ratio | 0.964 | 0.893 | 1.14 | 0.998 |
| Pilocarpine HCl 7.5mg | 7.4/7.4 | A → B | Papp | 24.7 | 22.9 | 21.8 | 23.1 |
| | | A → B | Recovery | 65.1% | 60.0% | 64.1% | 63.0% |
| | | B → A | Papp | 22.5 | 20.7 | 17.3 | 20.2 |
| | | B → A | Recovery | 75.0% | 82.9% | 79.1% | 79.2% |
| | | (B → A)/(A → B) | Efflux Ratio | 0.910 | 0.902 | 0.795 | 0.869 |

QC Criteria

All wells utilized for Papp determination in this study passed QC criteria for epithelial monolayer integrity. All of these wells exhibited Lucifer Yellow transport less than 2%.

All wells that were utilized in this assay for Papp determination exhibited TEER (Trans-Epithelial Electrical Resistance) readings greater than 1500 Ohms, also in accordance with QC criteria for acceptable monolayer integrity.

Summary and Conclusions

Figure 5A:
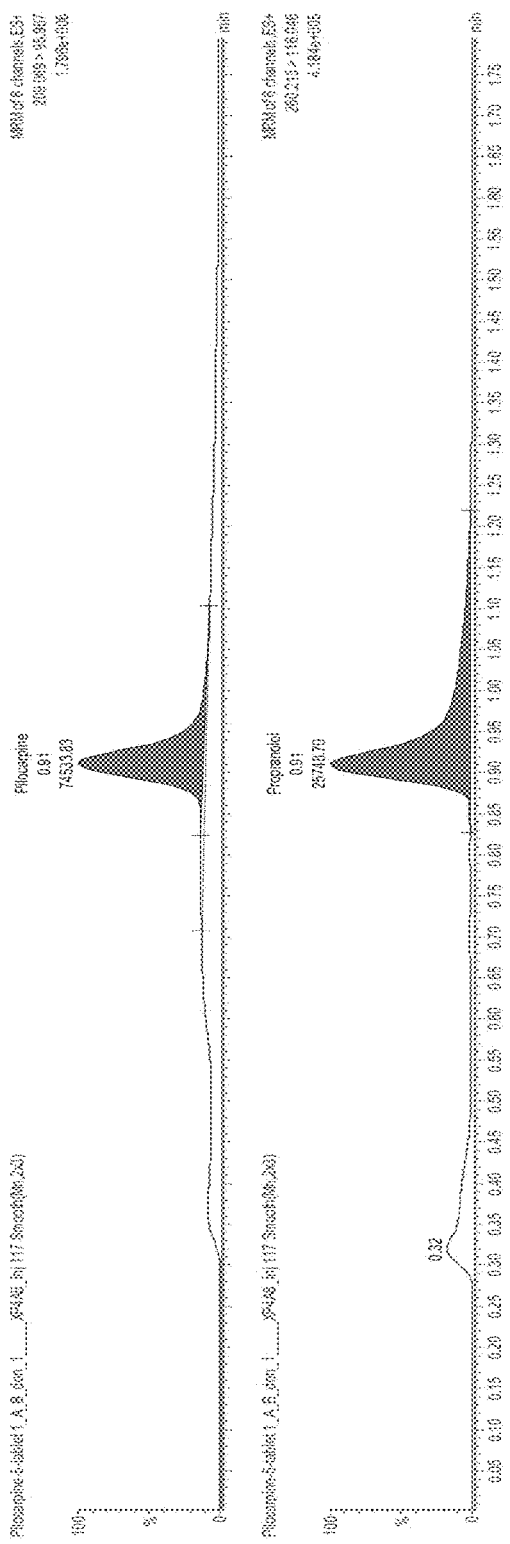
FIGS. 5A-5C show representative pilocarpine chromatograms. BCS high permeability control compound, metoprolol was used for FIGS. 5A-5C.
Figure 5B:
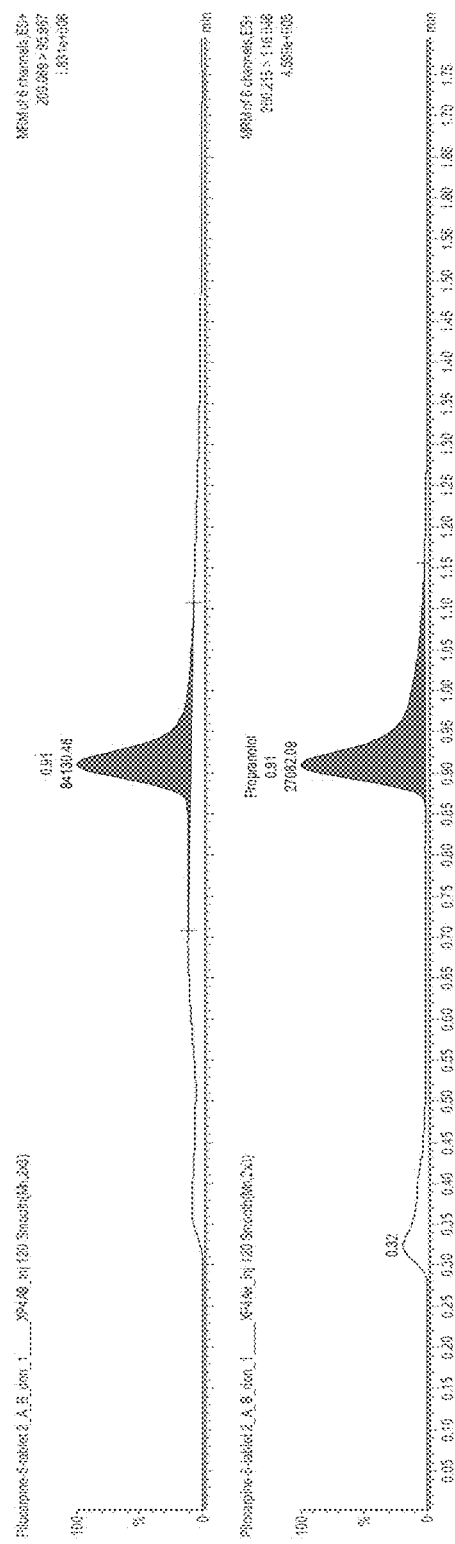
Figure 5C:
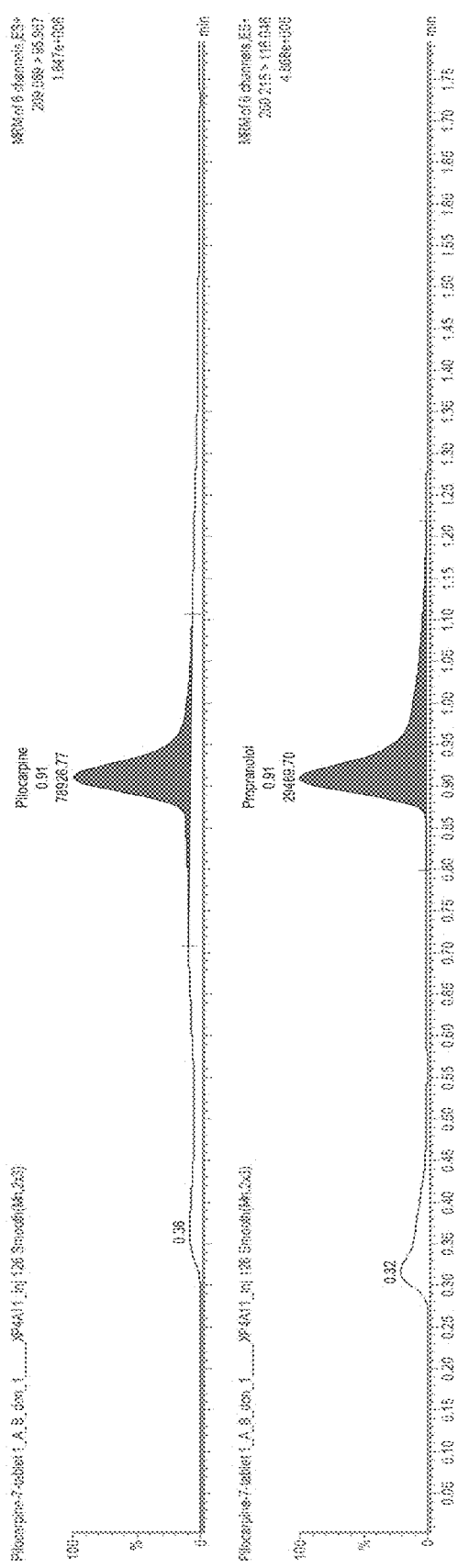

BCS criterion classifies pilocarpine as exhibiting high permeability across Caco-2 monolayers. All 3 batches of Pilocarpine tested in this study (liquid (FIG. 5C), 5.0 mg (FIG. 5A) tablet, and 7.5 mg tablet (FIG. 5B)) exhibited a very similar permeability profile at all 3 apical pH levels tested (Tables 17 and 18).

Propranolol is included in the solvent solution just prior to running samples on the HPLC-Mass spectrometer instruments. An analytical internal standard serves as a control against possible injection errors on the instrument during the run (i.e. if a needle gets clogged) and to ensure that ionization efficiency is not reduced during the instrument run. Representative chromatograms of propranolol were included (FIGS. 5A-5C) to show that the LC-MS/MS method, which was developed for pilocarpine, produced a symmetrical analyte peak (with peak area counts shown at the height of the peak, along with the retention time in minutes which is the x-axis) as well as showing the MRM transitions (parent→daughter) of the analyte in the upper right section of each chromatogram.

The apparent permeability rate coefficients (Papp) for all 3 batches of pilocarpine tested in this study (in the absorptive, A→B, transport direction) exceeds 90% of the Papp coefficient of the BCS high permeability control compound, metoprolol. Pilocarpine shows 97.4%, 114%, and 119% Papp values (relative to metoprolol) for liquid, 5.0 mg tablet, and 7.5 mg tablet, respectively. These values were measured at pH 7.4/7.4 conditions in this assay, for which the best post-assay recovery levels were seen.

These values meet the 90% threshold of FDA criteria for BCS classification as high permeability. As a result, all 3 batches of Pilocarpine tested in this study are classified as exhibiting high permeability for BCS purposes.

Pilocarpine oral solution permeability had not been tested previously. It was unexpected to see that the permeability of the oral solution was comparable to that of pilocarpine tablets.

REFERENCES

Stewart, B. H. et al. (1995). Comparison of intestinal permeabilities determined in multiple in vitro and in situ models: relationship to absorption in humans. Pharm. Res. 12:693-699.

Artursson, P. et al. (2001). Caco-2 monolayers in experimental and theoretical predictions of drug transport. Adv. Drug Deliv. Rev. 46:27-43.

Yee, Shiyin (1997). In Vitro Permeability across Caco-2 Cells (Colonic) Can Predict In Vivo (Small Intestinal) Absorption in Man—Fact or Myth. Pharm. Res 14(6): 763-766

Endres, C. J. et al. (2006). The role of transporters in drug interactions. Eur. J. Pharm. Sci. 27: 501-517.

Balimane, P. V. (2006). Current Industrial Practices of Assessing Permeability and P-Glycoprotein Interaction. AAPS J. 8(1):E1-E13.

Giacomini, K. M. et al. (2010). Membrane transporters in drug development. The International Transporter Consortium, White Paper. Nature Reviews Drug Discovery. 9:215-236.

Fawcett et al., Formulation and stability of pilocarpine oral solution. Article first published online: 22 Feb. 2011 DOI: 10.1111/j.2042-7174.1994.tb00780.x Ferguson M M et al. Pilocarpine oral solution. Br Dent J 1991; 170: 251.

Mehta A C, Hart-Davis S, Bedford C. Stability of pilocarpine oral solution. Hosp Pharm Pract 1992; 2 (11): 726-7.

While preferred embodiments of the present methods and compositions described herein have been shown, it will be obvious to those skilled in the art that such embodiments are provided by way of example only. Numerous variations, changes, and substitutions will now occur to those skilled in the art without departing from the methods and compositions described herein. It should be understood that various alternatives to the embodiments of the methods and compositions described herein may be employed in practicing the methods and compositions described herein. It is intended that the following claims define the scope of the methods and compositions described herein and that methods and structures within the scope of these claims and their equivalents be covered thereby.

What is claimed is:

1. A pharmaceutical solution or suspension suitable for oral administration comprising
   (i) pilocarpine; and
   (ii) a pharmaceutically acceptable solvent system comprising a glycol, a buffering agent, a sweetener, a flavoring agent, a preservative and a dye;
   wherein the solution comprises about 0.4-0.6% (w/v) citric acid (anhydrous); about 10-30% (w/v) glycerin; about 2-8% (w/v) propylene glycol; about 0.01-0.02% (w/v) sucralose; about 0.05-0.3% w/v hydroxyethylcellulose; about 0.25-0.75% w/v of poloxamer 407; about 0.05-0.2% w/v of simethicone emulsion; about 0.2-0.45% w/v of sodium citrate, dihydrate; about 0.1-0.2% w/v of sodium benzoate; and about 0.0004-0.0008% w/v of FD&C Blue No. 1.

2. The pharmaceutical solution or suspension of claim 1, wherein the flavoring agent is about 0.03-0.05% (w/v) Flavor Grape 59266/A and/or Flavor Cherry 825.662.

3. The pharmaceutical solution or suspension of claim 1, wherein the dye comprises about 0.0004-0.0008% w/v of FD&C Blue No. 1.

4. The pharmaceutical solution or suspension of claim 1, wherein the dye comprises about 0.001-0.003% w/v of FD&C Red No. 40.

5. The pharmaceutical solution or suspension of claim 1, wherein the solution comprises FD&C Blue No. 1 and FD&C Red No. 40.

6. The pharmaceutical solution or suspension of claim 1, wherein the solution comprises about 0.01-0.2% w/v of pilocarpine HCl.

7. The pharmaceutical solution or suspension of claim 1, wherein the solution comprises 0.1% w/v of pilocarpine HCl.

8. The pharmaceutical solution or suspension of claim 1, wherein the concentration of pilocarpine in the solution is 0.1 mg-2.0 mg/mL.

9. A pharmaceutical solution or suspension suitable for oral administration, comprising the following components:

| Ingredient | % w/v |
| --- | --- |
| Pilocarpine HCl | 0.1000 |
| Hydroxyethylcellulose | 0.2000 |
| Citric Acid, Anhydrous, USP | 0.5000 |
| FD&C Red No. 40 | 0.0015 |
| FD&C Blue No. 1 | 0.0005 |
| Flavor Grape 59266/A | 0.0400 |
| Glycerin, USP | 20.000 |
| Propylene Glycol, USP | 5.0000 |
| Poloxamer 407 | 0.5000 |
| Simethicone Emulsion | 0.0500 |
| Sodium Citrate, Dihydrate | 0.3500 |
| Sodium Benzoate, NF | 0.1500 |
| Sucralose, NF | 0.0150 |
| Sorbitol Solution 70% | 15.0000 |
| Purified Water, USP | QS |

10. The pharmaceutical solution or suspension of claim 1, wherein the solution or suspension does not comprise dyes.

11. The pharmaceutical solution or suspension of claim 1, wherein the solution has a viscosity in the range of 40-800 cps.

12. The pharmaceutical solution or suspension of claim 1, wherein the solution has a viscosity of 80-300 cps.

13. The pharmaceutical solution or suspension of claim 1, wherein the solution has a pH range from 3-6.

14. The pharmaceutical solution or suspension of claim 1, wherein the solution has a pH range from 3.5-5.5.

15. The pharmaceutical solution or suspension of claim 1, wherein the solution has a pH range from 4.2-4.8.

16. The pharmaceutical solution or suspension of claim 1, wherein the solution has less than 5% of any one degradant.

17. The pharmaceutical solution or suspension of claim 1, wherein the solution or suspension does not include boric acid.

18. The pharmaceutical solution or suspension of claim 1, wherein the solution or suspension does not include benzalkonium chloride.

19. The pharmaceutical solution or suspension of claim 1, wherein the solution or suspension is non-sterile.

20. A pharmaceutical solution or suspension suitable for oral administration comprising:

| Ingredient | mg/ml |
| --- | --- |
| Pilocarpine HCl | 1.000 |
| Hydroxyethylcellulose | 2.000 |
| Citric Acid, Anhydrous, USP | 5.000 |
| FD&C Red No. 40 | 0.015 |
| FD&C Blue No. 1 | 0.005 |
| Flavor Grape 59266/A | 0.400 |
| Glycerin, USP | 200.000 |
| Propylene Glycol, USP | 50.000 |
| Poloxamer 407 | 5.000 |
| Simethicone Emulsion | 0.500 |
| Sodium Citrate, Dihydrate | 3.500 |

-continued

| Ingredient | mg/ml |
|---|---|
| Sodium Benzoate, NF | 1.500 |
| Sucralose, NF | 0.150 |
| Purified Water, USP | QS |

* * * * *